United States Patent
Nettekoven et al.

(10) Patent No.: US 7,902,184 B2
(45) Date of Patent: Mar. 8, 2011

(54) PIPERAZINYL PYRIMIDINE DERIVATIVES

(75) Inventors: Matthias Heinrich Nettekoven, Grenzach-Wyhlen (DE); Olivier Roche, Folgensbourg (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 790 days.

(21) Appl. No.: 11/804,949

(22) Filed: May 21, 2007

(65) Prior Publication Data

US 2007/0281921 A1 Dec. 6, 2007

(30) Foreign Application Priority Data

May 30, 2006 (EP) .................................... 06114712

(51) Int. Cl.
*C07D 401/12* (2006.01)
*C07D 403/12* (2006.01)
*A61K 31/506* (2006.01)

(52) U.S. Cl. .......... 514/217.06; 514/252.14; 514/252.18; 514/252.19; 540/601; 544/295

(58) Field of Classification Search .................. 540/601; 544/295; 514/217.06, 252.14, 252.18, 252.19
See application file for complete search history.

(56) References Cited

U.S. PATENT DOCUMENTS

| | | | |
|---|---|---|---|
| 4,598,089 A | 7/1986 | Hadvary et al. | |
| 4,931,463 A | 6/1990 | Barbier et al. | |
| 4,983,746 A | 1/1991 | Barbier et al. | |
| 5,147,876 A * | 9/1992 | Mizuchi et al. ............... | 514/275 |
| 5,175,186 A | 12/1992 | Barbier et al. | |
| 5,246,960 A | 9/1993 | Barbier et al. | |
| 5,399,720 A | 3/1995 | Karpf et al. | |
| 6,004,996 A | 12/1999 | Shah et al. | |
| 2003/0105106 A1 | 6/2003 | Chiang et al. | |

FOREIGN PATENT DOCUMENTS

| | | |
|---|---|---|
| EP | 185 339 | 6/1986 |
| EP | 189 577 | 8/1986 |
| EP | 443 449 | 8/1991 |
| EP | 524 495 | 1/1993 |
| WO | WO 99/21834 A1 | 5/1999 |
| WO | WO 99/34786 | 7/1999 |
| WO | WO 00/09122 | 2/2000 |
| WO | WO 00/09123 | 2/2000 |
| WO | WO 00/58293 | 10/2000 |
| WO | WO 03/066604 A2 | 8/2003 |

OTHER PUBLICATIONS

Burks, T.F., Physiology of the Gastrointestinal Tract, Johnson L.R. ed., Raven Press, NY, pp. 211-242 (1994).
Leurs et al., Br J. Pharmacol., 102, pp. 179-185 (1991).
Raithel et al., Int. Arch. Allergy Immunol., 108, pp. 127-133 (1995).
Panula et al., Proc. Natl. Acad. Sci. USA, 81, pp. 2572-2576 (1984).
Inagaki et al., J. Comp. Neurol., 273, pp. 283-300 (1988).
Arrang et al., Nature, 302, pp. 832-837 (1983).
Arrang et al., Neuroscience, 23, pp. 149-157 (1987).
Clapham et al., Br. J. Pharmacol., 107, pp. 919-923 (1992).
Blandina et al. in The Histamine H3 Receptor (Leurs, R.L. and Timmermann, H. eds, pp. 27-40 (1998) Elsevier, Amsterdam, The Netherlands.
Masaki et al., Endocrinol., 144, pp. 2741-2748 (2003).
Hancock et al., European J. of Pharmacol., 487, pp. 183-197 (2004).
Timmermann, H., J. Med. Chem., 33, pp. 4-11 (1990).
Takahashi et al., J. Pharmacol. Exp. Therapeutics, 307, pp. 213-218 (2003).
Cheng et al., Biochem Pharmacol, 22, pp. 3099-3108 (1973).

* cited by examiner

*Primary Examiner* — Deepak Rao
(74) *Attorney, Agent, or Firm* — George W. Johnston; Dennis P. Tramaloni; Brian C. Remy

(57) ABSTRACT

The present invention relates to compounds of formula I and their pharmaceutically acceptable salts wherein formula I is:

$$
\text{Structure of Formula I showing a pyrimidine ring with substituents } X, Y, Z, \text{ an amide group } HN-C(=O)-R^2, \text{ and a piperazinyl group with } R^1
$$

wherein X, Y, Z, $R^1$ and $R^2$ are as defined in the description and claims. The compounds of the present invention act as antagonists and/or inverse agonists at the histamine 3 receptor and are useful for the treatment and/or prevention of diseases such as obesity, metabolic syndrome (syndrome X), and other eating disorders.

23 Claims, No Drawings

PIPERAZINYL PYRIMIDINE DERIVATIVES

PRIORITY TO RELATED APPLICATION(S)

This application claims the benefit of European Patent Application No. 06114712.0, filed May 30, 2006, which is hereby incorporated by reference in its entirety.

BACKGROUND OF THE INVENTION

The present invention is concerned with novel piperazinyl pyrimidine derivatives, their manufacture, pharmaceutical compositions containing them and their use as pharmaceutical compositions. The active compounds of the present invention are useful in treating obesity and other disorders. The compounds of the present invention are antagonists and/or inverse agonists at the histamine 3 receptor (H3 receptor).

Histamine (2-(4-imidazolyl)ethylamine) is one of the aminergic neurotransmitters which is widely distributed throughout the body, e.g. the gastrointestinal tract (Burks 1994 in Johnson L. R. ed., Physiology of the Gastrointestinal Tract, Raven Press, NY, pp. 211-242). Histamine regulates a variety of digestive pathophysiological events like gastric acid secretion, intestinal motility (Leurs et al., Br J. Pharmacol. 1991, 102, pp 179-185), vasomotor responses, intestinal inflammatory responses and allergic reactions (Raithel et al., Int. Arch. Allergy Immunol. 1995, 108, 127-133). In the mammalian brain, histamine is synthesized in histaminergic cell bodies which are found centrally in the tubero-mammillary nucleus of the posterior basal hypothalamus. From there, the histaminergic cell bodies project to various brain regions (Panula et al., Proc. Natl. Acad. Sci. USA 1984, 81, 2572-2576; Inagaki et al., J. Comp. Neurol 1988, 273, 283-300).

According to current knowledge, histamine mediates all its actions in both the CNS and the periphery through four distinct histamine receptors, the histamine H1, H2 H3 and H4 receptors. H3 receptors are predominantly localized in the central nervous system (CNS). As an autoreceptor H3 receptors constitutively inhibit the synthesis and secretion of histamine from histaminergic neurons (Arrang et al., Nature 1983, 302, 832-837; Arrang et al., Neuroscience 1987, 23, 149-157). As heteroreceptors, H3 receptors also modulate the release of other neurotransmitters such as acetylcholine, dopamine, serotonin and norepinephrine among others in both the central nervous system and in peripheral organs, such as lungs, cardiovascular system and gastrointestinal tract (Clapham & Kilpatrik, Br. J. Pharmacol. 1982, 107, 919-923; Blandina et al. in The Histamine H3 Receptor (Leurs R L and Timmermann H eds, 1998, pp 27-40, Elsevier, Amsterdam, The Netherlands). H3 receptors are constitutively active, meaning that even without exogenous histamine, the receptor is tonically activated. In the case of an inhibitory receptor such as the H3 receptor, this inherent activity causes tonic inhibition of neurotransmitter release. Therefore it may be important that a H3R antagonist would also have inverse agonist activity to both block exogenous histamine effects and to shift the receptor from its constitutively active (inhibitory) form to a neutral state.

The wide distribution of H3 receptors in the mammalian CNS indicates the physiological role of this receptor. Therefore the therapeutic potential as a novel drug development target in various indications has been proposed.

The administration of H3R ligands—as antagonists, inverse agonists, agonists or partial agonists—may influence the histamine levels or the secretion of neurotransmitters in the brain and the periphery and thus may be useful in the treatment of several disorders. Such disorders include obesity, (Masaki et al; Endocrinol. 2003, 144, 2741-2748; Hancock et al., European J. of Pharmacol. 2004, 487, 183-197), cardiovascular disorders such as acute myocardial infarction, dementia and cognitive disorders such as attention deficit hyperactivity disorder (ADHD) and Alzheimer's disease, neurological disorders such as schizophrenia, depression, epilepsy, Parkinson's disease, and seizures or convulsions, sleep disorders, narcolepsy, pain, gastrointestinal disorders, vestibular dysfunction such as Morbus Meniere, drug abuse and motion sickness (Timmermann, J. Med. Chem. 1990, 33, 4-11).

It is therefore an object of the present invention to provide selective, directly acting H3 receptor antagonists respectively inverse agonists. Such antagonists/inverse agonists are useful as therapeutically active substances, particularly in the treatment and/or prevention of diseases which are associated with the modulation of H3 receptors.

SUMMARY OF THE INVENTION

In particular, the present invention relates to the compounds of general formula I including all pharmaceutically acceptable salts thereof wherein formula I is:

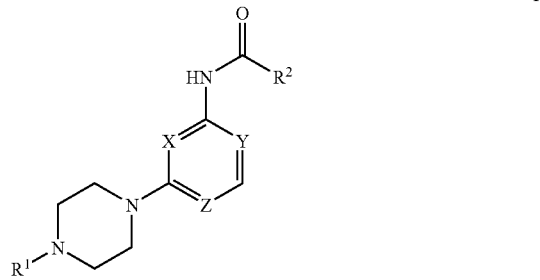

wherein X, Y, Z, $R^1$ and $R^2$ are as defined in the detailed description and claims.

The compounds of the present invention be used as pharmaceutical compositions for the treatment and/or prevention of diseases which are associated with the modulation of H3 receptors, such as obesity, metabolic syndrome (syndrome X), and other eating disorders.

DETAILED DESCRIPTION OF THE INVENTION

In the present description the term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower alkyl" or "$C_1$-$C_7$-alkyl", alone or in combination, signifies a straight-chain or branched-chain alkyl group with 1 to 7 carbon atoms. In preferred embodiments, the lower alkyl or $C_1$-$C_7$-alkyl is preferably a straight or branched-chain alkyl group with 1 to 6 carbon atoms, and more preferably with 1 to 4 carbon atoms. Examples of straight-chain and branched $C_1$-$C_7$ alkyl groups are methyl, ethyl, propyl, isopropyl, butyl, isobutyl, tert.-butyl, the isomeric pentyls, the isomeric hexyls and the isomeric heptyls, preferably methyl and ethyl, and most preferred methyl.

The term "cycloalkyl" or "$C_3$-$C_7$-cycloalkyl" denotes a saturated carbocyclic group containing from 3 to 7 carbon atoms, such as cyclopropyl, cyclobutyl, cyclopentyl, cyclohexyl or cycloheptyl. Especially preferred are cyclobutyl and cyclopentyl.

The term "alkoxy" or "lower alkoxy" refers to the group R'—O—, wherein R' is lower alkyl and the term "lower alkyl" has the previously given definition. Examples of lower alkoxy groups are, for example, methoxy, ethoxy, n-propoxy, isopropoxy, n-butoxy, isobutoxy, sec. butoxy and tert.-butoxy, preferably methoxy and ethoxy and most preferably methoxy.

The term "lower alkoxyalkyl" or "$C_1$-$C_7$-alkoxy-$C_1$-$C_7$-alkyl" refers to lower alkyl groups as defined previously wherein at least one of the hydrogen atoms of the lower alkyl groups is replaced by an alkoxy group (preferably methoxy or ethoxy). Among the preferred lower alkoxyalkyl groups are 2-methoxyethyl and 3-methoxypropyl.

The term "halogen" refers to fluorine, chlorine, bromine, or iodine. Preferred halogens are fluorine, chlorine and bromine.

The term "lower halogenalkyl" or "halogen-$C_1$-$C_7$-alkyl" refers to lower alkyl groups as defined previously wherein at least one of the hydrogen atoms of the lower alkyl group is replaced by a halogen atom (preferably fluoro or chloro, and most preferably fluoro). Among the preferred lower halogenalkyl groups are trifluoromethyl, difluoromethyl, trifluoroethyl, 2,2-difluoroethyl, fluoromethyl and chloromethyl, with trifluoromethyl or 2,2-difluoroethyl being especially preferred.

The term "lower phenylalkyl" or "phenyl-$C_{1-7}$-alkyl" refers to lower alkyl groups as defined previously wherein at least one of the hydrogen atoms of the lower alkyl group is replaced by a phenyl group. Preferred lower phenylalkyl groups are benzyl and phenethyl.

The term "N-heterocyclic ring" refers to heterocyclyl groups containing at least one nitrogen atom. Examples of "N-heterocyclic rings" include azetidinyl, pyrrolidinyl, imidazolidinyl, pyrazolidinyl, oxazolidinyl, isoxazolidinyl, thiazolidinyl, isothiazolidinyl, piperidinyl, piperazinyl, morpholinyl, thiomorpholinyl, and azepanyl, but also include partly unsaturated rings such as 2,5-dihydropyrrole. Preferred "N-heterocyclic rings" are azetidine, pyrrolidine, 2,5-dihydropyrrole, morpholine, piperazine, thiomorpholine, piperidine and azepane.

The term "form a 4-, 5-, 6- or 7-membered saturated heterocyclic ring optionally containing a further heteroatom of nitrogen, oxygen or sulfur" refers to a saturated N-heterocyclic ring, which may optionally contain a further nitrogen, oxygen or sulfur atom, such as azetidinyl, pyrrolidinyl, piperidinyl, piperazinyl, morpholinyl, thiomorpholinyl and azepanyl. A "4-, 5-, 6- or 7-membered partly unsaturated heterocyclic ring" means a heterocyclic ring as defined above which contains a double bond, for example 2,5-dihydropyrrolyl or 3,6-dihydro-2H-pyridinyl. The heterocyclic ring may be optionally substituted by one, two or three substituents independently selected from the group consisting of lower alkyl, lower alkoxy, hydroxy, halogen and halogenalkyl. The heterocyclic ring may also be condensed with a phenyl or a cyclohexyl ring, said phenyl or cyclohexyl ring being optionally substituted by one, two or three substituents independently selected from the group consisting of lower alkyl, lower alkoxy, hydroxy, halogen and halogenalkyl.

The term "said heterocyclic ring is optionally condensed with a phenyl or cyclohexyl ring" refers to a bicyclic ring system consisting of the heterocyclic ring and a phenyl or cyclohexyl ring both rings having one bond in common. Examples for such condensed heterocyclic rings are 3,4-dihydro-1H-isoquinoline, octahydroquinoline, 3,4-dihydro-2H-quinoline, 1,3-dihydroisoindole and 2,3-dihydroindole.

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 0.1 mg to about 5,000 mg, preferably from about 0.1 mg to about 1,000 mg, more preferably from about 0.5 to 500 mg, and more preferably from about 1 mg to 100 mg, should be appropriate, although the upper limit may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention are contemplated. Supplementary active compounds can also be incorporated into the compositions.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition, these salts may be prepared from addition of an inorganic base or an organic base to the free acid. Salts derived from an inorganic base include, but are not limited to, the sodium, potassium, lithium, ammonium, calcium, and magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compound of formula I can also be present in the form of zwitterions. Particularly preferred pharmaceutically acceptable salts of compounds of formula I are the hydrochloride salts.

The compounds of formula I can also be solvated, e.g. hydrated. The solvation can be effected in the course of the manufacturing process or can take place, for example, as a consequence of hygroscopic properties of an initially anhydrous compound of formula I (hydration). The term "pharmaceutically acceptable salts" also includes physiologically acceptable solvates.

"Isomers" are compounds that have identical molecular formulae but that differ in the nature or the sequence of bonding of their atoms or in the arrangement of their atoms in space. Isomers that differ in the arrangement of their atoms in space and have one or more asymmetric carbon atoms are termed "stereoisomers". Stereoisomers that are not mirror images of one another are termed "diastereoisomers", and stereoisomers that are non-superimposable mirror images are termed "enantiomers", or sometimes optical isomers.

In detail, the present invention relates to compounds of general formula I including all pharmaceutically acceptable salts thereof wherein formula I is:

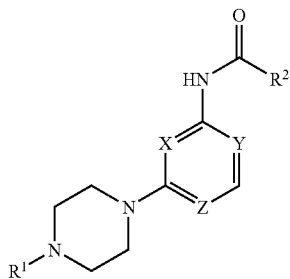

wherein:
(a) $R^1$ is lower alkyl or $C_3$-$C_7$-cycloalkyl;
(b) X, Y, and Z are defined in one of three groups selected from the group consisting of:
    (1) wherein X is N, Y is C and Z is N,
    (2) wherein X is N, Y is N and Z is C, and
    (3) wherein X is C, Y is N and Z is N;
(c) $R^2$ is selected from the group consisting of:
    (1) lower alkyl,
    (2) lower halogenalkyl,
    (3) lower hydroxyalkyl,
    (4) lower alkoxyalkyl,
    (5) $C_3$-$C_7$-cycloalkyl or $C_3$-$C_7$-cycloalkyl substituted by phenyl or lower alkyl,
    (6) lower $C_3$-$C_7$-cycloalkylalkyl,
    (7) unsubstituted phenyl or phenyl mono- or disubstituted by lower alkyl, lower alkoxy, halogen or lower halogenalkyl,
    (8) lower phenylalkyl wherein the phenyl ring is unsubstituted or mono- or disubstituted by lower alkyl, lower alkoxy, halogen or lower halogenalkyl,
    (9) unsubstituted pyridyl or pyridyl mono- or disubstituted by lower alkyl, lower alkoxy, halogen or lower halogenalkyl, and
    (10) —$NR^3R^4$;
(d) $R^3$ is hydrogen or lower alkyl, and $R^4$ is selected from the group consisting of:
    (1) lower alkyl,
    (2) lower alkoxyalkyl,
    (3) $C_3$-$C_7$-cycloalkyl or $C_3$-$C_7$-cycloalkyl substituted by phenyl,
    (4) lower $C_3$-$C_7$-cycloalkylalkyl,
    (5) unsubstituted phenyl or phenyl mono- or disubstituted by lower alkyl, lower alkoxy, halogen or lower halogenalkyl,
    (6) lower phenylalkyl wherein the phenyl ring is unsubstituted or mono- or disubstituted by lower alkyl, lower alkoxy, halogen or lower halogenalkyl, and
    (7) indanyl; or alternatively, $R^3$ and $R^4$ together with the nitrogen atom to which they are attached form a 4-, 5-, 6- or 7-membered saturated or partly unsaturated heterocyclic ring optionally containing a further heteroatom of nitrogen, oxygen or sulfur; wherein said heterocyclic ring is optionally substituted by one, two or three substituents independently selected from the group consisting of lower alkyl, lower alkoxy, hydroxy, halogen and halogenalkyl; or said heterocyclic ring is optionally condensed with a phenyl or cyclohexyl ring, wherein said phenyl or cyclohexyl ring is optionally substituted by one, two or three substituents independently selected from the group consisting of lower alkyl, lower alkoxy, hydroxy, halogen and halogenalkyl.

Preferred are compounds of formula I according to the present invention, wherein $R^1$ is $C_3$-$C_7$-cycloalkyl.

Also preferred are compounds of formula I according to the invention, wherein $R^1$ is ethyl or isopropyl.

Furthermore, the compounds of formula I according to present invention are preferred, wherein $R^2$ is —$NR^3R^4$ and $R^3$ and $R^4$ are as defined hereinbefore. Within this group, compounds of formula I are preferred, wherein $R^3$ is hydrogen or lower alkyl and $R^4$ is selected from the group consisting of:
    (1) lower alkyl,
    (2) lower alkoxyalkyl,
    (3) $C_3$-$C_7$-cycloalkyl or $C_3$-$C_7$-cycloalkyl substituted by phenyl,
    (4) lower $C_3$-$C_7$-cycloalkylalkyl,
    (5) unsubstituted phenyl or phenyl mono- or disubstituted by lower alkyl, lower alkoxy, halogen or lower halogenalkyl,
    (6) lower phenylalkyl wherein the phenyl ring is unsubstituted or mono- or disubstituted by lower alkyl, lower alkoxy, halogen or lower halogenalkyl, and
    (7) indanyl; or alternatively.

Also preferred are compounds of formula I according to the invention, wherein $R^3$ and $R^4$ together with the nitrogen atom to which they are attached form a 4-, 5-, 6- or 7-membered saturated or partly unsaturated heterocyclic ring optionally containing a further heteroatom selected from the group consisting of nitrogen, oxygen and sulfur, said heterocyclic ring is optionally substituted by one, two or three substituents independently selected from the group consisting of lower alkyl, lower alkoxy, hydroxy, halogen and halogenalkyl; or said heterocyclic ring is optionally condensed with a phenyl or cyclohexyl ring, wherein said phenyl or cyclohexyl ring is optionally substituted by one, two or three substituents independently selected from the group consisting of lower alkyl, lower alkoxy, hydroxy, halogen and halogenalkyl.

More preferred are compounds of formula I, wherein $R^3$ and $R^4$ together with the nitrogen atom to which they are attached form a heterocyclic ring selected from the group consisting of azetidine, pyrrolidine, 2,5-dihydropyrrole, morpholine, piperazine, thiomorpholine, piperidine and azepane, wherein said heterocyclic ring is optionally substituted by one, two or three substituents independently selected from the group consisting of lower alkyl, lower alkoxy, hydroxy, halogen and halogenalkyl, or said heterocyclic ring is optionally condensed with a phenyl or cyclohexyl ring, wherein said phenyl or cyclohexyl ring is optionally substituted by one, two or three substituents independently selected from the group consisting of lower alkyl, lower alkoxy, hydroxy, halogen and halogenalkyl.

Especially preferred are compounds of formula I according to the invention, wherein $R^3$ and $R^4$ together with the nitrogen atom to which they are attached form a heterocyclic ring selected from the group consisting of piperidine, pyrrolidine, 2,5-dihydropyrrole, azepane, 2,3-dihydroindole, 1,3-dihydroisoindole, octahydroquinoline, octahydroisoquinoline and morpholine, wherein said heterocyclic ring is optionally substituted by one, two or three substituents independently selected from the group consisting of lower alkyl, lower alkoxy, hydroxy, halogen and halogenalkyl.

Most preferably, compounds of formula I according to the present invention are those, wherein $R^3$ and $R^4$ together with the nitrogen atom to which they are attached form a heterocyclic ring selected from the group consisting of piperidine, 2-methylpiperidine, 3-methylpiperidine, 4-methylpiperidine, 3,5-dimethylpiperidine, 4-fluoropiperidine, 4-trifluoromethyl-piperidine, 3-hydroxypiperidine, 3,3-difluoropiperidine, 4,4-difluoropiperidine, pyrrolidine, 2-methylpyrrolidine, 2-isopropylpyrrolidine, 3-hydroxypyrrolidine, 2,5-dihydropyrrole, azepane, 2,3-dihydroindole, 1,3-dihydroisoindole, octahydroquinoline, octahydroisoquinoline, and morpholine.

Another group of preferred compounds of formula I are those, wherein $R^2$ is selected from the group consisting of:
(1) lower alkyl,
(2) lower halogenalkyl,
(3) lower hydroxyalkyl,
(4) lower alkoxyalkyl,
(5) $C_3$-$C_7$-cycloalkyl or $C_3$-$C_7$-cycloalkyl substituted by phenyl or lower alkyl,
(6) lower $C_3$-$C_7$-cycloalkylalkyl,
(7) unsubstituted phenyl or phenyl mono- or disubstituted by lower alkyl, lower alkoxy, halogen or lower halogenalkyl,
(8) lower phenylalkyl wherein the phenyl ring is unsubstituted or mono- or disubstituted by lower alkyl, lower alkoxy, halogen or lower halogenalkyl, and
(9) unsubstituted pyridyl or pyridyl mono- or disubstituted by lower alkyl, lower alkoxy, halogen or lower halogenalkyl.

Within this group, the compounds of formula I are more preferred, wherein $R^2$ is selected from the group consisting of:
(1) lower alkyl,
(2) lower alkoxyalkyl,
(3) $C_3$-$C_7$-cycloalkyl or $C_3$-$C_7$-cycloalkyl substituted by phenyl or lower alkyl,
(4) unsubstituted phenyl or phenyl mono- or disubstituted by lower alkyl, lower alkoxy, halogen or lower halogenalkyl, and
(5) lower phenylalkyl wherein the phenyl ring is unsubstituted or mono- or disubstituted by lower alkyl, lower alkoxy, halogen or lower halogenalkyl.

More preferred are the compounds of formula I, wherein $R^2$ is selected from the group consisting of:
(1) lower alkyl,
(2) lower alkoxyalkyl,
(3) $C_3$-$C_7$-cycloalkyl, and
(4) lower phenylalkyl wherein the phenyl ring is unsubstituted or mono- or disubstituted by lower alkyl, lower alkoxy, halogen or lower halogenalkyl.

In other preferred embodiments of the present invention, X is N, Y is C and Z is N. These are compounds of formula I having the formula I-i:

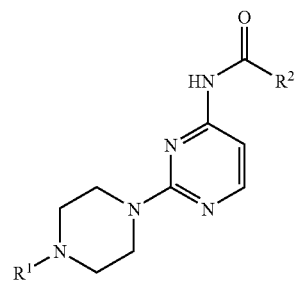

wherein $R^1$ and $R^2$ are as defined above.

Also preferred are the compounds of formula I wherein X is N, Y is N and Z is C. These are compounds of formula I having the formula I-ii:

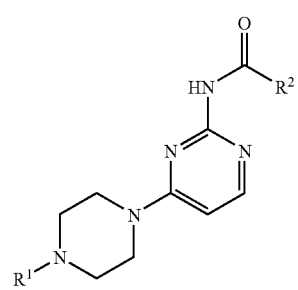

wherein $R^1$ and $R^2$ are as defined above.

Additionally preferred are compounds of formula I according to the present invention, wherein X is C, Y is N and Z is N. These are compounds of formula I having the formula I-iii:

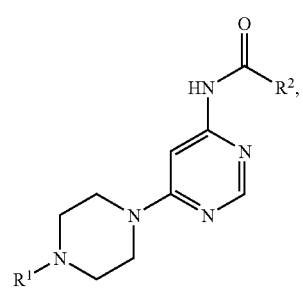

wherein $R^1$ and $R^2$ are as defined above.

In particular, preferred compounds of the present invention are selected from the group consisting of:
cyclopentanecarboxylic acid [2-(4-cyclopentyl-piperazin-1-yl)-pyrimidin-4-yl]-amide,
4,4-difluoro-piperidine-1-carboxylic acid [2-(4-cyclopentyl-piperazin-1-yl)-pyrimidin-4-yl]-amide,
cyclopentanecarboxylic acid [6-(4-ethyl-piperazin-1-yl)-pyrimidin-4-yl]-amide,
piperidine-1-carboxylic acid [6-(4-ethyl-piperazin-1-yl)-pyrimidin-4-yl]-amide,
2-(4-chloro-phenyl)-N-[2-(4-cyclopentyl-piperazin-1-yl)-pyrimidin-4-yl]-3-methyl-butyramide, azepane-1-carboxylic acid [2-(4-cyclopentyl-piperazin-1-yl)-pyrimidin-4-yl]-amide,
N-[4-(4-cyclopentyl-piperazin-1-yl)-pyrimidin-2-yl]-butyramide,
N-[4-(4-cyclopentyl-piperazin-1-yl)-pyrimidin-2-yl]-3-methyl-butyramide,
N-[4-(4-cyclopentyl-piperazin-1-yl)-pyrimidin-2-yl]-2-methoxy-acetamide,
cyclopentane carboxylic acid [4-(4-cyclopentyl-piperazin-1-yl)-pyrimidin-2-yl]-amide,
cyclohexane carboxylic acid [4-(4-cyclopentyl-piperazin-1-yl)-pyrimidin-2-yl]-amide,
N-[4-(4-cyclopentyl-piperazin-1-yl)-pyrimidin-2-yl]-4-methoxy-benzamide,
2-(4-chloro-phenyl)-N-[4-(4-cyclopentyl-piperazin-1-yl)-pyrimidin-2-yl]-3-methyl-butyramide,
N-[4-(4-isopropyl-piperazin-1-yl)-pyrimidin-2-yl]-butyramide,
N-[4-(4-isopropyl-piperazin-1-yl)-pyrimidin-2-yl]-3-methyl-butyramide,
cyclopentane carboxylic acid [4-(4-isopropyl-piperazin-1-yl)-pyrimidin-2-yl]-amide,
cyclohexane carboxylic acid [4-(4-isopropyl-piperazin-1-yl)-pyrimidin-2-yl]-amide,
4-fluoro-N-[4-(4-isopropyl-piperazin-1-yl)-pyrimidin-2-yl]-benzamide,
N-[4-(4-isopropyl-piperazin-1-yl)-pyrimidin-2-yl]-4-methoxy-benzamide,
N-[2-(4-cyclopentyl-piperazin-1-yl)-pyrimidin-4-yl]-butyramide,
N-[2-(4-cyclopentyl-piperazin-1-yl)-pyrimidin-4-yl]-3-methyl-butyramide,
cyclohexane carboxylic acid [2-(4-cyclopentyl-piperazin-1-yl)-pyrimidin-4-yl]-amide,
N-[2-(4-cyclopentyl-piperazin-1-yl)-pyrimidin-4-yl]-4-fluoro-benzamide,
N-[6-(4-ethyl-piperazin-1-yl)-pyrimidin-4-yl]-4-fluoro-benzamide,
cyclopentane carboxylic acid [6-(4-isopropyl-piperazin-1-yl)-pyrimidin-4-yl]-amide,
N-[6-(4-isopropyl-piperazin-1-yl)-pyrimidin-4-yl]-3-methyl-butyramide,
N-[6-(4-isopropyl-piperazin-1-yl)-pyrimidin-4-yl]-butyramide,
4-fluoro-N-[6-(4-isopropyl-piperazin-1-yl)-pyrimidin-4-yl]-benzamide,
2-ethyl-N-[6-(4-isopropyl-piperazin-1-yl)-pyrimidin-4-yl]-butyramide,
cyclopentane carboxylic acid [6-(4-cyclopentyl-piperazin-1-yl)-pyrimidin-4-yl]-amide,
N-[6-(4-cyclopentyl-piperazin-1-yl)-pyrimidin-4-yl]-3-methyl-butyramide,
N-[6-(4-cyclopentyl-piperazin-1-yl)-pyrimidin-4-yl]-butyramide,
N-[6-(4-cyclopentyl-piperazin-1-yl)-pyrimidin-4-yl]-4-fluoro-benzamide,
N-[6-(4-cyclopentyl-piperazin-1-yl)-pyrimidin-4-yl]-3-fluoro-benzamide,
N-[6-(4-cyclopentyl-piperazin-1-yl)-pyrimidin-4-yl]-2-fluoro-benzamide,
N-[6-(4-cyclopentyl-piperazin-1-yl)-pyrimidin-4-yl]-2-ethyl-butyramide,
2-methyl-pentanoic acid [6-(4-cyclopentyl-piperazin-1-yl)-pyrimidin-4-yl]-amide,
pyrrolidine-1-carboxylic acid [6-(4-ethyl-piperazin-1-yl)-pyrimidin-4-yl]-amide,
4-methyl-piperidine-1-carboxylic acid [6-(4-ethyl-piperazin-1-yl)-pyrimidin-4-yl]-amide,
2,3-dihydro-indole-1-carboxylic acid [6-(4-ethyl-piperazin-1-yl)-pyrimidin-4-yl]-amide,
azepane-1-carboxylic acid [6-(4-ethyl-piperazin-1-yl)-pyrimidin-4-yl]-amide,
2-methyl-pyrrolidine-1-carboxylic acid [6-(4-ethyl-piperazin-1-yl)-pyrimidin-4-yl]-amide,
3-methyl-piperidine-1-carboxylic acid [6-(4-ethyl-piperazin-1-yl)-pyrimidin-4-yl]-amide,
octahydro-isoquinoline-2-carboxylic acid [6-(4-ethyl-piperazin-1-yl)-pyrimidin-4-yl]-amide,
1,3-dihydro-isoindole-2-carboxylic acid [6-(4-ethyl-piperazin-1-yl)-pyrimidin-4-yl]-amide,
1-cyclopropylmethyl-3-[6-(4-ethyl-piperazin-1-yl)-pyrimidin-4-yl]-urea,
1-[6-(4-ethyl-piperazin-1-yl)-pyrimidin-4-yl]-3-(2-methoxy-ethyl)-urea,
1-(1,2-dimethyl-propyl)-3-[6-(4-ethyl-piperazin-1-yl)-pyrimidin-4-yl]-urea,
1-cyclopentyl-3-[6-(4-ethyl-piperazin-1-yl)-pyrimidin-4-yl]-urea,
1-[6-(4-ethyl-piperazin-1-yl)-pyrimidin-4-yl]-3-[1-(4-fluoro-phenyl)-ethyl]-urea,
1-[6-(4-ethyl-piperazin-1-yl)-pyrimidin-4-yl]-3-indan-1-yl-urea,
1-[6-(4-ethyl-piperazin-1-yl)-pyrimidin-4-yl]-3-(4-fluoro-benzyl)-urea,
1-[6-(4-ethyl-piperazin-1-yl)-pyrimidin-4-yl]-3-(4-fluoro-phenyl)-urea,
piperidine-1-carboxylic acid [6-(4-isopropyl-piperazin-1-yl)-pyrimidin-4-yl]-amide,
morpholine-4-carboxylic acid [6-(4-isopropyl-piperazin-1-yl)-pyrimidin-4-yl]-amide,
pyrrolidine-1-carboxylic acid [6-(4-isopropyl-piperazin-1-yl)-pyrimidin-4-yl]-amide,
4-methyl-piperidine-1-carboxylic acid [6-(4-isopropyl-piperazin-1-yl)-pyrimidin-4-yl]-amide,
2,3-dihydro-indole-1-carboxylic acid [6-(4-isopropyl-piperazin-1-yl)-pyrimidin-4-yl]-amide,
azepane-1-carboxylic acid [6-(4-isopropyl-piperazin-1-yl)-pyrimidin-4-yl]-amide,
2-methyl-pyrrolidine-1-carboxylic acid [6-(4-isopropyl-piperazin-1-yl)-pyrimidin-4-yl]-amide,
3-methyl-piperidine-1-carboxylic acid [6-(4-isopropyl-piperazin-1-yl)-pyrimidin-4-yl]-amide,
octahydro-isoquinoline-2-carboxylic acid [6-(4-isopropyl-piperazin-1-yl)-pyrimidin-4-yl]-amide,
1,3-dihydro-isoindole-2-carboxylic acid [6-(4-isopropyl-piperazin-1-yl)-pyrimidin-4-yl]-amide,
1-cyclopropylmethyl-3-[6-(4-isopropyl-piperazin-1-yl)-pyrimidin-4-yl]-urea,
1-[6-(4-isopropyl-piperazin-1-yl)-pyrimidin-4-yl]-3-propyl-urea,
1-[6-(4-isopropyl-piperazin-1-yl)-pyrimidin-4-yl]-3-(2-methoxy-ethyl)-urea,
1-(1,2-dimethyl-propyl)-3-[6-(4-isopropyl-piperazin-1-yl)-pyrimidin-4-yl]-urea,
1-cyclopentyl-3-[6-(4-isopropyl-piperazin-1-yl)-pyrimidin-4-yl]-urea,
1-[1-(4-fluoro-phenyl)-ethyl]-3-[6-(4-isopropyl-piperazin-1-yl)-pyrimidin-4-yl]-urea,
1-indan-1-yl-3-[6-(4-isopropyl-piperazin-1-yl)-pyrimidin-4-yl]-urea,
1-[6-(4-isopropyl-piperazin-1-yl)-pyrimidin-4-yl]-3-(2-methoxy-phenyl)-urea, 1-(4-fluoro-benzyl)-3-[6-(4-isopropyl-piperazin-1-yl)-pyrimidin-4-yl]-urea,
1-(4-fluoro-phenyl)-3-[6-(4-isopropyl-piperazin-1-yl)-pyrimidin-4-yl]-urea,
2-methyl-pyrrolidine-1-carboxylic acid [6-(4-cyclopentyl-piperazin-1-yl)-pyrimidin-4-yl]-amide,
3-methyl-piperidine-1-carboxylic acid [6-(4-cyclopentyl-piperazin-1-yl)-pyrimidin-4-yl]-amide,
1-cyclohexyl-3-[6-(4-cyclohexyl-piperazin-1-yl)-pyrimidin-4-yl]-1-isopropyl-urea,
piperidine-1-carboxylic acid [6-(4-cyclohexyl-piperazin-1-yl)-pyrimidin-4-yl]-amide,
pyrrolidine-1-carboxylic acid [6-(4-cyclohexyl-piperazin-1-yl)-pyrimidin-4-yl]-amide,
morpholine-4-carboxylic acid [6-(4-cyclohexyl-piperazin-1-yl)-pyrimidin-4-yl]-amide,
3-methyl-piperidine-1-carboxylic acid [6-(4-cyclohexyl-piperazin-1-yl)-pyrimidin-4-yl]-amide,
1-cyclohexyl-3-[6-(4-cyclohexyl-piperazin-1-yl)-pyrimidin-4-yl]-urea,
azepane-1-carboxylic acid [6-(4-cyclohexyl-piperazin-1-yl)-pyrimidin-4-yl]-amide,
2-methyl-piperidine-1-carboxylic acid [6-(4-cyclohexyl-piperazin-1-yl)-pyrimidin-4-yl]-amide,
1-[6-(4-cyclohexyl-piperazin-1-yl)-pyrimidin-4-yl]-3-cyclopentyl-urea,
2-isopropyl-pyrrolidine-1-carboxylic acid [6-(4-cyclohexyl-piperazin-1-yl)-pyrimidin-4-yl]-amide,
4-methyl-piperidine-1-carboxylic acid [6-(4-cyclohexyl-piperazin-1-yl)-pyrimidin-4-yl]-amide,
octahydro-quinoline-1-carboxylic acid [6-(4-cyclohexyl-piperazin-1-yl)-pyrimidin-4-yl]-amide,
3-hydroxy-pyrrolidine-1-carboxylic acid [6-(4-cyclohexyl-piperazin-1-yl)-pyrimidin-4-yl]-amide,
4,4-difluoro-piperidine-1-carboxylic acid [6-(4-cyclohexyl-piperazin-1-yl)-pyrimidin-4-yl]-amide,
3,3-difluoro-piperidine-1-carboxylic acid [6-(4-cyclohexyl-piperazin-1-yl)-pyrimidin-4-yl]-amide,
2,5-dihydro-pyrrole-1-carboxylic acid [6-(4-cyclohexyl-piperazin-1-yl)-pyrimidin-4-yl]-amide,
3-hydroxy-piperidine-1-carboxylic acid [6-(4-cyclohexyl-piperazin-1-yl)-pyrimidin-4-yl]-amide,
3,5-dimethyl-piperidine-1-carboxylic acid [6-(4-cyclohexyl-piperazin-1-yl)-pyrimidin-4-yl]-amide,
4-trifluoromethyl-piperidine-1-carboxylic acid [6-(4-cyclohexyl-piperazin-1-yl)-pyrimidin-4-yl]-amide,
3-[6-(4-cyclohexyl-piperazin-1-yl)-pyrimidin-4-yl]-1,1-diethyl-urea,
4-fluoro-piperidine-1-carboxylic acid [6-(4-cyclohexyl-piperazin-1-yl)-pyrimidin-4-yl]-amide,
1-cyclohexyl-3-[6-(4-cyclopentyl-piperazin-1-yl)-pyrimidin-4-yl]-1-isopropyl-urea,
piperidine-1-carboxylic acid [6-(4-cyclopentyl-piperazin-1-yl)-pyrimidin-4-yl]-amide,
pyrrolidine-1-carboxylic acid [6-(4-cyclopentyl-piperazin-1-yl)-pyrimidin-4-yl]-amide,
morpholine-4-carboxylic acid [6-(4-cyclopentyl-piperazin-1-yl)-pyrimidin-4-yl]-amide,
1,3-dihydro-isoindole-2-carboxylic acid [6-(4-cyclopentyl-piperazin-1-yl)-pyrimidin-4-yl]-amide,
1-cyclohexyl-3-[6-(4-cyclopentyl-piperazin-1-yl)-pyrimidin-4-yl]-urea,
azepane-1-carboxylic acid [6-(4-cyclopentyl-piperazin-1-yl)-pyrimidin-4-yl]-amide,
2-methyl-piperidine-1-carboxylic acid [6-(4-cyclopentyl-piperazin-1-yl)-pyrimidin-4-yl]-amide,
1-cyclopentyl-3-[6-(4-cyclopentyl-piperazin-1-yl)-pyrimidin-4-yl]-urea,
2-isopropyl-pyrrolidine-1-carboxylic acid [6-(4-cyclopentyl-piperazin-1-yl)-pyrimidin-4-yl]-amide,
4-methyl-piperidine-1-carboxylic acid [6-(4-cyclopentyl-piperazin-1-yl)-pyrimidin-4-yl]-amide,
octahydro-quinoline-1-carboxylic acid [6-(4-cyclopentyl-piperazin-1-yl)-pyrimidin-4-yl]-amide,
3-hydroxy-pyrrolidine-1-carboxylic acid [6-(4-cyclopentyl-piperazin-1-yl)-pyrimidin-4-yl]-amide,
4,4-difluoro-piperidine-1-carboxylic acid [6-(4-cyclopentyl-piperazin-1-yl)-pyrimidin-4-yl]-amide,
3,3-difluoro-piperidine-1-carboxylic acid [6-(4-cyclopentyl-piperazin-1-yl)-pyrimidin-4-yl]-amide,
4-methoxy-piperidine-1-carboxylic acid [6-(4-cyclopentyl-piperazin-1-yl)-pyrimidin-4-yl]-amide,
2,5-dihydro-pyrrole-1-carboxylic acid [6-(4-cyclopentyl-piperazin-1-yl)-pyrimidin-4-yl]-amide,
3-hydroxy-piperidine-1-carboxylic acid [6-(4-cyclopentyl-piperazin-1-yl)-pyrimidin-4-yl]-amide,
3,5-dimethyl-piperidine-1-carboxylic acid [6-(4-cyclopentyl-piperazin-1-yl)-pyrimidin-4-yl]-amide,
4-trifluoromethyl-piperidine-1-carboxylic acid [6-(4-cyclopentyl-piperazin-1-yl)-pyrimidin-4-yl]-amide,
1-[6-(4-cyclopentyl-piperazin-1-yl)-pyrimidin-4-yl]-3-propyl-urea,
3-[6-(4-cyclopentyl-piperazin-1-yl)-pyrimidin-4-yl]-1,1-diethyl-urea,
4-fluoro-piperidine-1-carboxylic acid [6-(4-cyclopentyl-piperazin-1-yl)-pyrimidin-4-yl]-amide, and
any pharmaceutically acceptable salt thereof.

Especially preferred are the compounds of formula I selected from the group consisting of:
4,4-difluoro-piperidine-1-carboxylic acid [2-(4-cyclopentyl-piperazin-1-yl)-pyrimidin-4-yl]-amide,
azepane-1-carboxylic acid [2-(4-cyclopentyl-piperazin-1-yl)-pyrimidin-4-yl]-amide,
4-methyl-piperidine-1-carboxylic acid [6-(4-ethyl-piperazin-1-yl)-pyrimidin-4-yl]-amide,
2-methyl-pyrrolidine-1-carboxylic acid [6-(4-ethyl-piperazin-1-yl)-pyrimidin-4-yl]-amide,
3-methyl-piperidine-1-carboxylic acid [6-(4-ethyl-piperazin-1-yl)-pyrimidin-4-yl]-amide,
1-cyclopentyl-3-[6-(4-ethyl-piperazin-1-yl)-pyrimidin-4-yl]-urea,
piperidine-1-carboxylic acid [6-(4-isopropyl-piperazin-1-yl)-pyrimidin-4-yl]-amide,
pyrrolidine-1-carboxylic acid [6-(4-isopropyl-piperazin-1-yl)-pyrimidin-4-yl]-amide,
4-methyl-piperidine-1-carboxylic acid [6-(4-isopropyl-piperazin-1-yl)-pyrimidin-4-yl]-amide,
azepane-1-carboxylic acid [6-(4-isopropyl-piperazin-1-yl)-pyrimidin-4-yl]-amide,
2-methyl-pyrrolidine-1-carboxylic acid [6-(4-isopropyl-piperazin-1-yl)-pyrimidin-4-yl]-amide,
3-methyl-piperidine-1-carboxylic acid [6-(4-isopropyl-piperazin-1-yl)-pyrimidin-4-yl]-amide,
1-cyclopentyl-3-[6-(4-isopropyl-piperazin-1-yl)-pyrimidin-4-yl]-urea,
2-methyl-pyrrolidine-1-carboxylic acid [6-(4-cyclopentyl-piperazin-1-yl)-pyrimidin-4-yl]-amide,
3-methyl-piperidine-1-carboxylic acid [6-(4-cyclopentyl-piperazin-1-yl)-pyrimidin-4-yl]-amide,
piperidine-1-carboxylic acid [6-(4-cyclohexyl-piperazin-1-yl)-pyrimidin-4-yl]-amide,
3-methyl-piperidine-1-carboxylic acid [6-(4-cyclohexyl-piperazin-1-yl)-pyrimidin-4-yl]-amide, azepane-1-carboxylic acid [6-(4-cyclohexyl-piperazin-1-yl)-pyrimidin-4-yl]-amide,
2-methyl-piperidine-1-carboxylic acid [6-(4-cyclohexyl-piperazin-1-yl)-pyrimidin-4-yl]-amide,
4-methyl-piperidine-1-carboxylic acid [6-(4-cyclohexyl-piperazin-1-yl)-pyrimidin-4-yl]-amide,
octahydro-quinoline-1-carboxylic acid [6-(4-cyclohexyl-piperazin-1-yl)-pyrimidin-4-yl]-amide,
3,5-dimethyl-piperidine-1-carboxylic acid [6-(4-cyclohexyl-piperazin-1-yl)-pyrimidin-4-yl]-amide,
4-fluoro-piperidine-1-carboxylic acid [6-(4-cyclohexyl-piperazin-1-yl)-pyrimidin-4-yl]-amide,
1-cyclohexyl-3-[6-(4-cyclopentyl-piperazin-1-yl)-pyrimidin-4-yl]-1-isopropyl-urea,
piperidine-1-carboxylic acid [6-(4-cyclopentyl-piperazin-1-yl)-pyrimidin-4-yl]-amide,
pyrrolidine-1-carboxylic acid [6-(4-cyclopentyl-piperazin-1-yl)-pyrimidin-4-yl]-amide,
1,3-dihydro-isoindole-2-carboxylic acid [6-(4-cyclopentyl-piperazin-1-yl)-pyrimidin-4-yl]-amide,
1-cyclohexyl-3-[6-(4-cyclopentyl-piperazin-1-yl)-pyrimidin-4-yl]-urea,
azepane-1-carboxylic acid [6-(4-cyclopentyl-piperazin-1-yl)-pyrimidin-4-yl]-amide,
2-methyl-piperidine-1-carboxylic acid [6-(4-cyclopentyl-piperazin-1-yl)-pyrimidin-4-yl]-amide,
1-cyclopentyl-3-[6-(4-cyclopentyl-piperazin-1-yl)-pyrimidin-4-yl]-urea,
4-methyl-piperidine-1-carboxylic acid [6-(4-cyclopentyl-piperazin-1-yl)-pyrimidin-4-yl]-amide,
octahydro-quinoline-1-carboxylic acid [6-(4-cyclopentyl-piperazin-1-yl)-pyrimidin-4-yl]-amide,
4,4-difluoro-piperidine-1-carboxylic acid [6-(4-cyclopentyl-piperazin-1-yl)-pyrimidin-4-yl]-amide,
2,5-dihydro-pyrrole-1-carboxylic acid [6-(4-cyclopentyl-piperazin-1-yl)-pyrimidin-4-yl]-amide,
3,5-dimethyl-piperidine-1-carboxylic acid [6-(4-cyclopentyl-piperazin-1-yl)-pyrimidin-4-yl]-amide,
4-fluoro-piperidine-1-carboxylic acid [6-(4-cyclopentyl-piperazin-1-yl)-pyrimidin-4-yl]-amide, and
any pharmaceutically acceptable salt thereof.

Furthermore, the pharmaceutically acceptable salts of the compounds of formula I and the pharmaceutically acceptable esters of the compounds of formula I individually constitute preferred embodiments of the present invention.

Compounds of formula I may form acid addition salts with acids, such as conventional pharmaceutically acceptable acids, for example hydrochloride, hydrobromide, phosphate, acetate, fumarate, maleate, salicylate, sulphate, pyruvate, citrate, lactate, mandelate, tartarate, and methanesulphonate. Preferred are the hydrochloride salts. Also solvates and hydrates of compounds of formula I and their salts form part of the present invention.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbents or eluant). The invention embraces all of these forms.

It will be appreciated, that the compounds of general formula I in this invention may be derivatized at functional groups to provide derivatives which are capable of conversion back to the parent compound in vivo. Physiologically acceptable and metabolically labile derivatives, which are capable of producing the parent compounds of general formula I in vivo are also within the scope of this invention.

A further aspect of the present invention is the process for the manufacture of compounds of formula I as defined above, which process comprises:

(a) reacting a compound of the formula II:

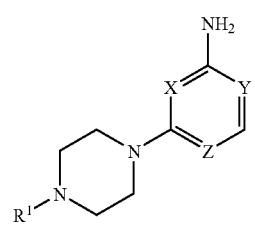

wherein X, Y, Z and $R^1$ are as defined previously, with a chloride of the formula III:

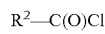

wherein $R^2$ is as defined previously, to obtain a compound of the formula I-A:

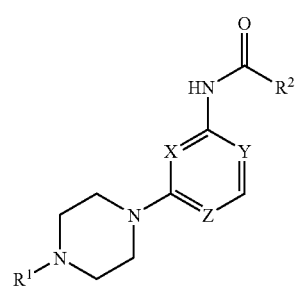

wherein X, Y, Z, $R^1$ and $R^2$ are as defined previously, or (b) activating a compound of the formula II:

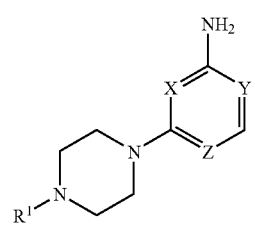

wherein X, Y, Z and $R^1$ are as defined previously, with phenylchloroformate or di-tert-butyl dicarbonate to obtain a carbamate ester of formula IV:

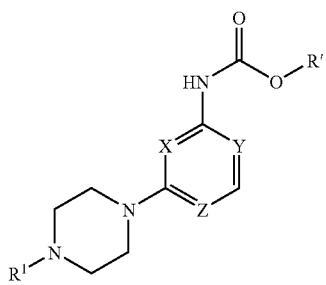

IV wherein R' is phenyl or tert-butyl, respectively, which is then reacted with an amine of formula V:

H—NR³R⁴  V, wherein R³ and R⁴ are as defined hereinbefore, to obtain a compound of the formula I-B:

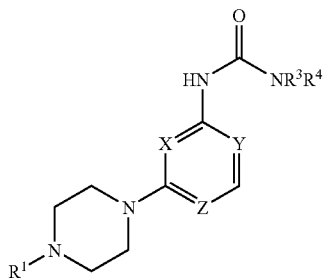

I-B wherein X, Y, Z, R¹, R³ and R⁴ are as defined previously, or (c) activating a compound of the formula II:

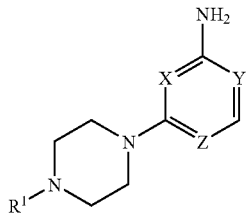

II wherein X, Y, Z and R¹ are as defined previously, with phenylchloroformate or di-tert-butyl dicarbonate to obtain a carbamate ester of formula IV:

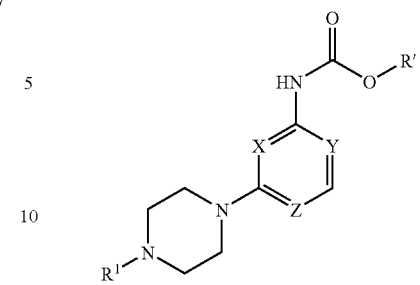

IV wherein R' is phenyl or tert-butyl, respectively, which is then reacted with a chloride of the formula III:

$$R^2—C(O)Cl \quad\quad III$$

wherein R² is as defined previously, to obtain a compound of the formula I-C:

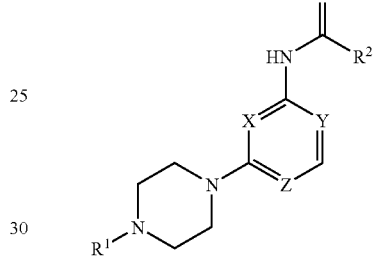

I-C wherein X, Y, Z, R¹ and R² are as defined previously, and (d) optionally converting the compound of formula I-A, I-B or I-C into a pharmaceutically acceptable salt.

In more detail, the compounds of formula I can be manufactured by the methods given below, by the methods given in the examples or by analogous methods. Appropriate reaction conditions for the individual reaction steps are known to a person skilled in the art. Starting materials are either commercially available or can be prepared by methods analogous to the methods given below, by methods described in references cited in the text or in the examples, or by methods known in the art.

The preparation of compounds of formula I of the present invention may be carried out in sequential or convergent synthetic routes. Syntheses of the invention are shown in the following scheme. The skills required for carrying out the reaction and purification of the resulting products are known to those in the art. The substituents and indices used in the following description of the processes have the significance given herein before unless indicated to the contrary.

Scheme 1

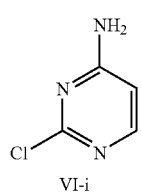

VI-i

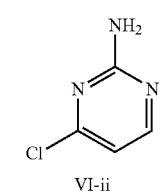

VI-ii

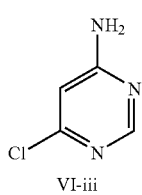

VI-iii

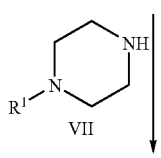

VII

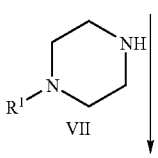

VII

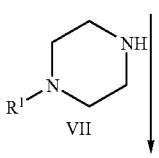

VII

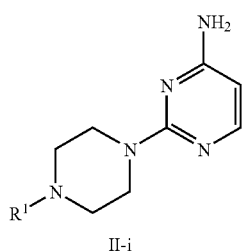
II-i

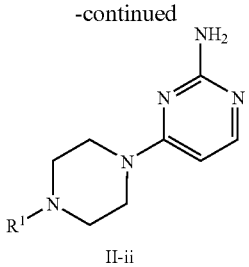
II-ii

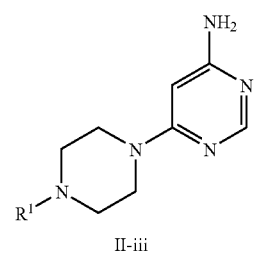
II-iii

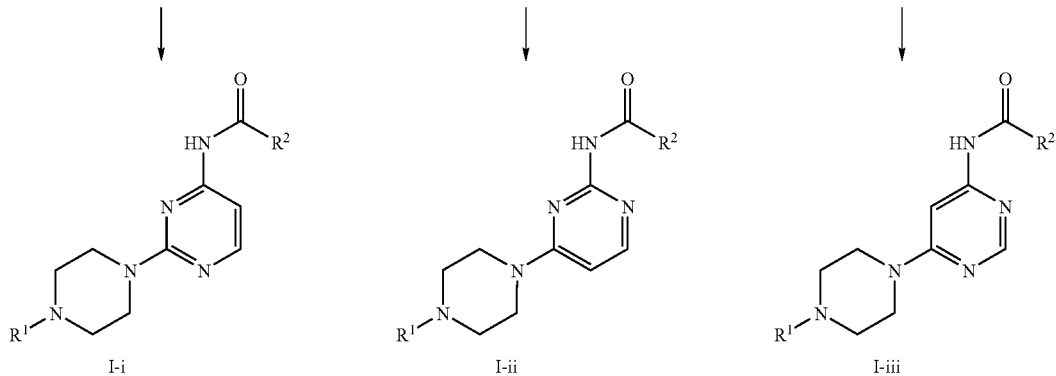

I-i

I-ii

I-iii

Compounds of general formula I can be prepared according to scheme 1 as follows:

a) The coupling of chloro substituted pyrimidine derivatives with piperazines is widely described in literature and the procedures are known to those in the art (for reaction conditions described in literature affecting such reactions see for example: Comprehensive Organic Transformations: A Guide to Functional Group Preparations, 2nd Edition, Richard C. Larock. John Wiley & Sons, New York, N.Y. 1999). 2-Chloro-4-pyrimidinylamine (VI-i), 2-amino-4-chloro-pyrimidine (VI-ii) or 4-amino-2-chloropyrimidine (VI-iii) can conveniently be transformed to the respective pyrimidine derivatives II-i, II-ii or II-iii, respectively, through reaction with a piperazine derivative of formula VII (either commercially available or accessible by methods described in references or by methods known in the art; as appropriate). The reaction can be carried out in the presence or the absence of a solvent and in the presence or the absence of a base. We find it convenient to carry out the reaction in a solvent like water and/or dimethylformamide (DMF). There is no particular restriction on the nature of the solvent to be employed, provided that it has no adverse effect on the reaction or the reagents involved and that it can dissolve the reagents, at least to some extent. Examples for suitable solvents include DMF, dichloromethane (DCM), dioxane, tetrahydrofurane (THF), and the like. There is no particular restriction on the nature of the base used in this stage, and any base commonly used in this type of reaction may equally be employed here. Examples of such bases include triethylamine and diisopropyl-ethylamine, and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. A period of from 0.5 h to several days will usually suffice to yield pyrimidine derivatives II-i, II-ii or II-iii.

b) Amides, carbamates and ureas can be prepared from suitable starting materials according to methods known in the art. The conversion of the amino-moiety in II-i, II-ii or II-iii to access amides, carbamates and ureas can be affected by methods described in literature. For example the conversion of the amine derivatives II to access compounds of the general formula I is affected by reaction of II with suitable acid chlorides of formula III, chloroformates, or carbonate esters, respectively, in a solvent like dichloromethane and in the presence or the absence of a base. The compounds of formula III, chloroformates or carbonate esters are commercially available or can be prepared by known methods. There is no particular restriction on the nature of the solvent to be employed, provided that it has no adverse effect on the reaction or the reagents involved and that it can dissolve the reagents, at least to some extent. Examples for suitable solvents include chloroform, or dioxane, THF, and the like. There is no particular restriction on the nature of the base used in this stage, and any base commonly used in this type of reaction may equally be employed here. Examples of such bases include triethylamine and diisopropyl-ethylamine, and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield pyrimidine derivatives of formula I. For reaction conditions described in literature affecting such reactions see for example: Comprehensive Organic Transformations: A Guide to Functional Group Preparations, 2nd Edition, Richard C. Larock. John Wiley & Sons, New York, N.Y. 1999.

In order to obtain compounds of formula I wherein $R^2$ is —$NR^3R^4$, as defined herein before, II can be activated under various conditions known to those in the art. However we find it convenient to activate the amine functionality in II with phenylchloroformate in order to access the respective phenylcarbamate of formula IV. The reaction can be carried out in the presence or the absence of a solvent and/or a base. There is no particular restriction on the nature of the solvent to be employed, provided that it has no adverse effect on the reaction or the reagents involved and that it can dissolve the reagents, at least to some extent. Examples for suitable solvents include dichlormethane (DCM), chloroform, THF, and the like. There is no particular restriction on the nature of the base used in this stage, and any base commonly used in this type of reaction may equally be employed here. Examples of such bases include pyridine, triethylamine and diisopropylethylamine, and the like. The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield the intermediate phenylcarbamate. Subsequently, the reaction mixture is treated with an amine of formula V (HNR$^3$R$^4$, as defined herein before). The reaction can take place over a wide range of temperatures, and the precise reaction temperature is not critical to the invention. We find it convenient to carry out the reaction with heating from ambient temperature to reflux. The time required for the reaction may also vary widely, depending on many factors, notably the reaction temperature and the nature of the reagents. However, a period of from 0.5 h to several days will usually suffice to yield compounds of formula I.

The compounds of formula I can contain several asymmetric centers and can be present in the form of optically pure enantiomers, mixtures of enantiomers such as, e.g. racemates, optically pure diastereomers, mixtures of diastereomers, diastereomeric racemates or mixtures of diastereomeric racemates. The optically active forms can be obtained for example by resolution of the racemates, by asymmetric synthesis or asymmetric chromatography (chromatography with a chiral adsorbent or eluant).

As described above, the compounds of formula I of the present invention can be used as pharmaceutical compositions for the treatment and/or prevention of diseases which are associated with the modulation of H3 receptors.

In this context, the expression 'diseases associated with the modulation of H3 receptors' means diseases which can be treated and/or prevented by modulation of H3 receptors. Such diseases encompass, but are not limited to, obesity, metabolic syndrome (syndrome X), neurological diseases including Alzheimer's disease, dementia, age-related memory dysfunction, mild cognitive impairment, cognitive deficit, attention deficit hyperactivity disorder, epilepsy, neuropathic pain, inflammatory pain, migraine, Parkinson's disease, multiple sclerosis, stroke, dizziness, schizophrenia, depression, addiction, motion sickness and sleep disorders including narcolepsy, and other diseases including asthma, allergy, allergy-induced airway responses, congestion, chronic obstructive pulmonary disease and gastro-intestinal disorders.

In a preferable aspect, the expression 'diseases associated with modulation of H3 receptors' relates to obesity, metabolic syndrome (syndrome X), and other eating disorders, with obesity being especially preferred.

The invention therefore also relates to pharmaceutical compositions comprising a compound as defined above and a pharmaceutically acceptable carrier and/or adjuvant.

Further, the invention relates to compounds as defined above for use as therapeutically active substances, particularly as therapeutic active substances for the treatment and/or prevention of diseases which are associated with the modulation of H3 receptors.

In another embodiment, the invention relates to a method for the treatment and/or prevention of diseases which are associated with the modulation of H3 receptors, which method comprises administering a therapeutically active amount of a compound of formula I to a human being or animal. A method for the treatment and/or prevention of obesity is preferred.

The invention further relates to the use of compounds of formula I as defined above for the treatment and/or prevention of diseases which are associated with the modulation of H3 receptors.

In addition, the invention relates to the use of compounds of formula I as defined above for the preparation of pharmaceutical compositions for the treatment and/or prevention of diseases which are associated with the modulation of H3 receptors. The use of compounds of formula I as defined above for the preparation of pharmaceutical compositions for the treatment and/or prevention of obesity is preferred.

Furthermore, the present invention relates to the use of a compound of formula I for the manufacture of a pharmaceutical composition for the treatment and prevention of obesity in a patient who is also receiving treatment with a lipase inhibitor and particularly, wherein the lipase inhibitor is orlistat.

It is a further preferred object of the present invention to provide a method for the treatment or prevention of obesity and obesity related disorders which comprises administration of a therapeutically effective amount of a compound according to formula I in combination or association with a therapeutically effective amount of other drugs for the treatment of obesity or eating disorders so that together they give effective relief. Suitable other drugs include, but are not limited to, anorectic agents, lipase inhibitors, selective serotonin reuptake inhibitors (SSRI) and agents that stimulate metabolism of body fat. Combinations or associations of the above agents may be encompassing separate, sequential or simultaneous administration.

The term "lipase inhibitor" refers to compounds which are capable of inhibiting the action of lipases, for example gastric and pancreatic lipases. For example orlistat and lipstatin as described in U.S. Pat. No. 4,598,089 are potent inhibitor of lipases. Lipstatin is a natural product of microbial origin, and orlistat is the result of a hydrogenation of lipstatin. Other lipase inhibitors include a class of compound commonly referred to as panclicins. Panclicins are analogues of orlistat (Mutoh et al, 1994). The term "lipase inhibitor" refers also to polymer bound lipase inhibitors for example described in International Patent Application WO 99/34786 (Geltex Pharmaceuticals Inc.). These polymers are characterized in that they have been substituted with one or more groups that inhibit lipases. The term "lipase inhibitor" also comprises pharmaceutically acceptable salts of these compounds. The term "lipase inhibitor" preferably refers to tetrahydrolipstatin. Administration of a therapeutically effective amount of a compound according to formula I in combination or association with a therapeutically effective amount of tetrahydrolipstatin is especially preferred.

Tetrahydrolipstatin (orlistat) is a known compound useful for the control or prevention of obesity and hyperlipidemia.

See, U.S. Pat. No. 4,598,089, issued Jul. 1, 1986, which also discloses processes for making orlistat and U.S. Pat. No. 6,004,996, which discloses appropriate pharmaceutical compositions. Further suitable pharmaceutical compositions are described for example in International Patent Applications WO 00/09122 and WO 00/09123. Additional processes for the preparation of orlistat are disclosed in European Patent Applications Publication Nos. 0 185 359, 0 189 577, 0 443 449, and 0 524 495.

Suitable anorectic agents of use in combination with a compound of the present invention include, but are not limited to, APD356, aminorex, amphechloral, amphetamine, axokine, benzphetamine, bupropion, chlorphentermine, clobenzorex, cloforex, clominorex, clortermine, CP945598, cyclexedrine, CYT009-GhrQb, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, metreleptin, norpseudoephedrine, pentorex, phendimetrazine, phenmetrazine, phentermine, phenylpropanolamine, picilorex, rimonabant, sibutramine, SLV319, SNAP 7941, SR147778 (Surinabant), steroidal plant extract (e.g. P57) and TM30338 and pharmaceutically acceptable salts thereof.

Most preferable anorectic agents are sibutramine, rimonabant and phentermine.

Suitable selective serotonin reuptake inhibitors of use in combination with a compound of the present invention include: fluoxetine, fluvoxamine, paroxetine and sertraline, and pharmaceutically acceptable salts thereof.

Suitable agents that stimulate metabolism of body fat include, but are not limited to, growth hormone agonist (e.g. AOD-9604).

The use of a compound of formula I in the manufacture of a pharmaceutical composition for the treatment and prevention of obesity in a patient who is also receiving treatment with a compound selected from the group consisting of a lipase inhibitor, an anorectic agent, a selective serotonin reuptake inhibitor, and an agent that stimulates metabolism of body fat, is also an object of the present invention.

The use of a compound of formula I in the manufacture of a pharmaceutical composition for the treatment and prevention of obesity in a patient who is also receiving treatment with a lipase inhibitor, preferably with tetrahydrolipstatin, is also an object of the present invention.

It is a further preferred object to provide a method of treatment or prevention of Type II diabetes (non-insulin dependent diabetes mellitus (NIDDM)) in a human which comprises administration of a therapeutically effective amount of a compound according to formula I in combination or association with a therapeutically effective amount of a lipase inhibitor, particularly, wherein the lipase inhibitor is tetrahydrolipstatin. Also an object of the invention is the method as described above for the simultaneous, separate or sequential administration of a compound according to formula I and a lipase inhibitor, particularly tetrahydrolipstatin.

It is a further preferred object to provide a method of treatment or prevention of Type II diabetes (non-insulin dependent diabetes mellitus (NIDDM)) in a human which comprises administration of a therapeutically effective amount of a compound according to formula I in combination or association with a therapeutically effective amount of an anti-diabetic agent.

The term "anti-diabetic agent" refers to compounds selected from the group consisting of 1) PPARγ agonists such as pioglitazone (actos) or rosiglitazone (avandia), and the like; 2) biguanides such as metformin (glucophage), and the like; 3) sulfonylureas such as glibenclamide, glimepiride (amaryl), glipizide (glucotrol), glyburide (DiaBeta), and the like; 4) nonsulfonylureas such as nateglinide (starlix), repaglimide (prandin), and the like; 5) PPARα/γ agonists such as GW-2331, and the like 6) DPP-IV-inhibitors such as LAF-237 (vildagliptin), MK-0431, BMS-477118 (saxagliptin) or GSK23A and the like; 7) Glucokinase activators such as the compounds disclosed in e.g. WO 00/58293 A1, and the like; 8) α-Glucosidase inhibitors such as acarbose (precose) or miglitol (glyset), and the like.

Also an object of the invention is the method as described above for the simultaneous, separate or sequential administration of a compound according to formula I and a therapeutically effective amount of an anti-diabetic agent.

The use of a compound of formula I in the manufacture of a pharmaceutical composition for the treatment and prevention of Type II diabetes in a patient who is also receiving treatment with an anti-diabetic agent is also an object of the present invention.

It is a further preferred object to provide a method of treatment or prevention of dyslipidemias in a human which comprises administration of a therapeutically effective amount of a compound according to formula I in combination or association with a therapeutically effective amount of a lipid lowering agent.

The term "lipid lowering agent" refers to compounds selected from the group consisting of 1) bile acid sequestrants such as cholestyramine (questran), colestipol (colestid), and the like; 2) HMG-CoA reductase inhibitors such as atorvastatin (lipitor), cerivastatin (baycol), fluvastatin (lescol), pravastatin (pravachol), simvastatin (zocor) and the like; 3) cholesterol absorption inhibitors such as ezetimibe, and the like; 4) CETP inhibitors such as torcetrapib, JTT 705, and the like; 5) PPARα-agonists such as beclofibrate, gemfibrozil (lopid), fenofibrate (lipidil), bezafibrate (bezalip), and the like; 6) lipoprotein synthesis inhibitors such as niacin, and the like; and 7) niacin receptor agonists such as nicotinic acid, and the like.

Also an object of the invention is the method as described above for the simultaneous, separate or sequential administration of a compound according to formula I and a therapeutically effective amount of a lipid lowering agent.

The use of a compound of formula I in the manufacture of a pharmaceutical composition for the treatment and prevention of dyslipidemias in a patient who is also receiving treatment with a lipid lowering agent, is also an object of the present invention.

It is a further preferred object to provide a method of treatment or prevention of hypertension in a human which comprises administration of a therapeutically effective amount of a compound according to formula I in combination or association with a therapeutically effective amount of an anti-hypertensive agent.

The term "anti-hypertensive agent" or "blood-pressure lowering agent" refers to compounds selected from the group consisting of 1) Angiotensin-converting Enzyme (ACE) Inhibitors including benazepril (lotensin), captopril (capoten), enalapril (vasotec), fosinopril (monopril), lisinopril (prinivil, zestril), moexipril (univasc), perindopril (coversum), quinapril (accupril), ramipril (altace), trandolapril (mavik), and the like; 2) Angiotensin II Receptor Antagonists including candesartan (atacand), eprosartan (teveten), irbesartan (avapro), losartan (cozaar), telmisartan (micadisc), valsartan (diovan), and the like; 3) Adrenergic Blockers (peripheral or central) such as the beta-adrenergic blockers including acebutolol (sectrol), atenolol (tenormin), betaxolol (kerlone), bisoprolol (zebeta), carteolol (cartrol), metoprolol (lopressor; toprol-XL), nadolol (corgard), penbutolol (levatol), pindolol (visken), propranolol (inderal), timolol (blockadren) and the like; alpha/beta adrenergic blockers including carvedilol (coreg), labetalol (normodyne), and the like; alpha-1 adrenergic blockers including prazosin (minipress), doxazosin (cardura), terazosin (hytrin), phenoxybenzamine (dibenzyline), and the like; peripheral adrenergic-neuronal blockers including guanadrel (hylorel), guanethidine (ismelin), reserpine (serpasil), and the like; alpha-2 adrenergic blockers including a-methyldopa (aldomet), clonidine (catapres), guanabenz (wytensin), guanfacine (tenex), and the like; 4) Blood Vessel Dilators (Vasodilators) including hydralazine (apresoline), minoxidil (lonitren), clonidine (catapres), and the like; 5) Calcium Channel Blockers including amlodipine (norvasc), felodipine (plendil), isradipine (dynacirc), nicardipine (cardine sr), nifedipine (procardia, adalat), nisoldipine (sular), diltiazem (cardizem), verapamil (isoptil), and the like; 6) Diuretics such as thiazides and thiazides-like agents, including hydrochlorothiazide (hydrodiuril, microzide), chlorothiazide (diuril), chlorthalidone (hygroton), indapamide (lozol), metolazone (mykrox), and the like; loop diuretics, such as bumetamide (bumex) and furosemide (lasix), ethacrynic acid (edecrin), torsemide (demadex), and the like; potassium-sparing diuretics including amiloride (midamor), triamterene (dyrenium), spironolactone (aldactone), and the tiamenidine (symcor) and the like; 7) Tyrosine Hydroxylase Inhibitors, including metyrosine (demser), and the like; 8) Neutral Endopeptidase Inhibitors, including BMS-186716 (omapatrilat), UK-79300 (candoxatril), ecadotril (sinorphan), BP-1137 (fasidotril), UK-79300 (sampatrilat) and the like; and 9) Endothelin Antagonists including tezosentan, A308165, and the like.

Also an object of the invention is the method as described above for the simultaneous, separate or sequential administration of a compound according to formula I and a therapeutically effective amount of a anti-hypertensive agent.

The use of a compound of formula I in the manufacture of a pharmaceutical composition for the treatment and prevention of hypertension in a patient who is also receiving treatment with an anti-hypertensive agent, is also an object of the present invention.

As described above, the compounds of formula I and their pharmaceutically acceptable salts possess valuable pharmacological properties. Specifically, it has been found that the compounds of the present invention are good histamine 3 receptor (H3R) antagonists and/or inverse agonists.

The following test was carried out in order to determine the activity of the compounds of formula I.

Binding Assay with $^3$H—(R)α-methylhistamine

Saturation binding experiments were performed using HR3-CHO membranes prepared as described in Takahashi, K, Tokita, S., Kotani, H. (2003) J. Pharmacol. Exp. Therapeutics 307, 213-218.

An appropriate amount of membrane (60 to 80 µg protein/well) was incubated with increasing concentrations of $^3$H(R)α-methylhistamine di-hydrochloride (0.10 to 10 nM). Non specific binding was determined using a 200 fold excess of cold (R)α-methylhistamine dihydrobromide (500 nM final concentration). The incubation was carried out at room temperature (in deep-well plates shaking for three hours). The final volume in each well was 250 µl. The incubation was followed by rapid filtration on GF/B filters (pre-soaked with 100 µl of 0.5% PEI in Tris 50 mM shaking at 200 rpm for two hours). The filtration was made using a cell-harvester and the filter plates were then washed five times with ice cold washing buffer containing 0.5 M NaCl. After harvesting, the plates were dried at 55° C. for 60 min, then scintillation fluid (Microscint 40, 40 microl in each well) was added and the amount of radioactivity on the filter was determined in Packard topcounter after shaking the plates for two hours at 200 rpm at room temperature.

Binding Buffer: 50 mM Tris-HCl pH 7.4 and 5 mM $MgCl_2 \times 6H_2O$ pH 7.4. Washing Buffer: 50 mM Tris-HCl pH 7.4 and 5 mM $MgCl_2 \times 6H_2O$ and 0.5 M NaCl pH 7.4.

Indirect measurement of affinity of H3R inverse agonists: twelve increasing concentrations (ranging from 10 µM to 0.3 nM) of the selected compounds were always tested in competition binding experiments using membrane of the human H3R-CHO cell line. An appropriate amount of protein, e.g. approximately 500 cpm binding of RAMH at Kd, were incubated for 1 hour at room temperature in 250 µl final volume in 96-well plates in presence of $^3$H(R)α-methylhistamine (1 nM final concentration=Kd). Non-specific binding was determined using a 200 fold excess of cold (R)α-Methylhistamine dihydrobromide.

All compounds were tested at a single concentration in duplicate. Compounds that showed an inhibition of [$^3$H]-RAMH by more than 50% were tested again to determine $IC_{50}$ in a serial dilution experiment, meaning concentrations were spanning 10 points starting from $4.6 \times 10^{-6}$ M to $1.0 \times 10^{-9}$ M. The dilution factor was 1/2.15 for the whole series. The concentration at which 50% inhibition of the radioligand $^3$H(R)α-methylhistamine is obtained (the $IC_{50}$) is determined from the linear regression of a plot of the logarithm of the concentration versus percent inhibition measured for the different concentrations. Ki's were calculated from $IC_{50}$ based on Cheng-Prusoff equation (Cheng, Y, Prusoff, W H (1973) Biochem Pharmacol 22, 3099-3108): Ki=IC50/[1+D/Kd] wherein D is the concentration of the radioligand and Kd is the binding constant for the radioligand binding to the receptor and the conditions used in the competition experiment.

The compounds of the present invention exhibit $K_i$ values within the range of about 1 nM to about 1000 nM, preferably of about 1 nM to about 100 nM, and more preferably of about 1 nM to about 50 nM. The following table shows measured values for some selected compounds of the present invention.

|  | $K_i$ (nM) |
| --- | --- |
| Example 6 | 51.0 |
| Example 54 | 34.6 |
| Example 93 | 22.2 |

Demonstration of additional biological activities of the compounds of the present invention may be accomplished through in vitro, ex vivo, and in vivo assays that are well known in the art. For example, to demonstrate the efficacy of a pharmaceutical agent for the treatment of obesity-related disorders such as diabetes, Syndrome X, or atherosclerotic disease and related disorders such as hypertriglyceridemia and hypercholesteremia, the following assays may be used.

Method for Measuring Blood Glucose Levels db/db mice (obtained from Jackson Laboratories, Bar Harbor, Me.) are bled (by either eye or tail vein) and grouped according to equivalent mean blood glucose levels. They are dosed orally (by gavage in a pharmaceutically acceptable vehicle) with the test compound once daily for 7 to 14 days. At this point, the animals are bled again by eye or tail vein and blood glucose levels are determined.

Method for Measuring Triglyceride Levels hApoAl mice (obtained from Jackson Laboratories, Bar Harbor, Me.) are bled (by either eye or tail vein) and grouped according to equivalent mean serum triglyceride levels. They are dosed orally (by gavage in a pharmaceutically acceptable vehicle) with the test compound once daily for 7 to 14 days. The animals are then bled again by eye or tail vein, and serum triglyceride levels are determined.

Method for Measuring HDL-Cholesterol Levels

To determine plasma HDL-cholesterol levels, hApoAl mice are bled and grouped with equivalent mean plasma HDL-cholesterol levels. The mice are orally dosed once daily with vehicle or test compound for 7 to 14 days, and then bled on the following day. Plasma is analyzed for HDL-cholesterol.

The compounds of formula I and their pharmaceutically acceptable salts and esters can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical preparations can be effected in a manner which will be familiar to any person skilled in the art by bringing the described compounds of formula I and their pharmaceutically acceptable, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 1 mg to about 100 mg, comes into consideration. Depending on the dosage it is convenient to administer the daily dosage in several dosage units.

The pharmaceutical preparations conveniently contain about 0.1-500 mg, preferably 0.5-100 mg, of a compound of formula I.

The following are a list of abbreviations and/or acronyms with their corresponding definitions used in the examples below: THF refers to tetrahydrofurane; DMF refers to N,N-dimethylformamide; DCM refers to dichloromethane; $NEt_3$ refers to triethylamine; $AlMe_3$ refers to trimethylaluminum; HPLC refers to high-performance liquid chromatography; MS(m/e) refers to mass spectrometry (m/e=mass to charge ratio); and $MH^+$ is a term used in mass spectrometry and refers to molecular weight plus hydrogen.

The following examples serve to illustrate the present invention in more detail. They are, however, not intended to limit its scope in any manner.

EXAMPLES

Example 1

Cyclopentanecarboxylic acid [2-(4-cyclopentyl-piperazin-1-yl)-pyrimidin-4-yl]-amide a) Step 1: 2-(4-Cyclopentyl-piperazin-1-yl)-pyrimidin-4-ylamine (Intermediate 1)

A mixture of 0.5 g (3.86 mmol) 2-chloro-4-pyrimidinylamine (commercially available) and 1-cyclopentyl-piperazine (commercially available) in 1 mL DMF was heated to 70° C. for 16 h. The residue after filtration washed with diethyl ether and dried to yield 0.49 g (51%) of the title compound (intermediate 1) as white solid. MS (m/e): 284.3 ($MH^+$).

b) Step 2: Cyclopentanecarboxylic acid [2-(4-cyclopentyl-piperazin-1-yl)-pyrimidin-4-yl]-amide (Procedure A)

A mixture of 10 mg (0.04 mmol) 2-(4-cyclopentyl-piperazin-1-yl)-pyrimidin-4-ylamine, 10.8 mg (0.082 mmol) cyclopentylcarbonyl chloride and 13.5 mg (0.12 mmol) potassium t-butoxide in 0.7 mL THF was shaken at room temperature for 16 h. The mixture was treated with water and methanol and subjected to preparative HPLC purification on reversed phase eluting with a gradient of acetonitrile/water (0.05% triethylamine). The combined product fractions were evaporated to dryness to yield 3 mg (21%) of the title compound as white solid. MS (m/e): 344.1 ($MH^+$).

Intermediate 2

4-(4-Cyclopentyl-piperazin-1-yl)-pyrimidin-2-ylamine

According to the procedure described for the synthesis of intermediate 1 the title compound was synthesized from 2-amino-4-chloro-pyrimidine (commercially available) and 1-cyclopentyl piperazine (commercially available). MS (m/e): 248.3 ($MH^+$).

Intermediate 3

4-(4-Isopropyl-piperazin-1-yl)-pyrimidin-2-ylamine

According to the procedure described for the synthesis of intermediate 1 the title compound was synthesized from 2-amino-4-chloro-pyrimidine (commercially available) and 1-isopropyl piperazine (commercially available). MS (m/e): 222.1 (MH$^+$).

Intermediate 4

6-(4-Ethyl-piperazin-1-yl)-pyrimidin-4-ylamine

A mixture of 1 g (7.7 mmol) 4-amino-6-chloropyrimidine (commercially available) and 1.75 g (15.4 mmol) 1-ethyl piperazine (commercially available) in 10 mL toluene was heated to 110° C. for 16 h. After evaporation of all volatiles the residue was purified by flash column chromatography on silica eluting with a gradient formed from DCM (0.5% NEt$_3$) and methanol. The combined product fractions were evaporated to dryness to yield the title compound. MS (m/e): 208.3 (MH$^+$).

Intermediate 5

6-(4-Isopropyl-piperazin-1-yl)-pyrimidin-4-ylamine

According to the procedure described for the synthesis of intermediate 4 the title compound was synthesized from 4-amino-6-chloropyrimidine (commercially available) and 1-isopropyl piperazine (commercially available). MS (m/e): 222.4 (MH$^+$).

Intermediate 6

6-(4-Cyclopentyl-piperazin-1-yl)-pyrimidin-4-ylamine

According to the procedure described for the synthesis of intermediate 4 the title compound was synthesized from 4-amino-6-chloropyrimidine (commercially available) and 1-cyclopentyl piperazine (commercially available). MS (m/e): 248.4 (MH$^+$).

Intermediate 7

6-(4-Cyclohexyl-piperazin-1-yl)-pyrimidin-4-ylamine

According to the procedure described for the synthesis of intermediate 4 the title compound was synthesized from 4-amino-6-chloropyrimidine (commercially available) and 1-cyclohexyl piperazine (commercially available). MS (m/e): 262.0 (MH$^+$).

Example 2

4,4-Difluoro-piperidine-1-carboxylic acid [2-(4-cyclopentyl-piperazin-1-yl)-pyrimidin-4-yl]-amide Procedure B:
A mixture of 103 mg (0.42 mmol) 2-(4-cyclopentyl-piperazin-1-yl)-pyrimidin-4-ylamine (intermediate 1), 67 mg (0.428 mmol) phenyl chloroformate (commercially available) and 0.1 g (0.12 mmol) pyridine in 4 mL DCM was shaken for 30 min at room temperature. A fraction of this mixture containing 0.07 mmol of the intermediately built [2-(4-cyclopentyl-piperazin-1-yl)-pyrimidin-4-yl]-carbamic acid phenyl ester was treated with 64.8 mg (0.41 mmol) 4,4-difluoro-piperidine, hydrochloride and 0.05 mL NEt$_3$. The mixture was shaken at room temperature and concentrated. Methanol, DMF and water were added and the mixture was subjected to preparative HPLC purification on reversed phase eluting with a gradient of acetonitrile/water (0.05% triethylamine). The combined product fractions were evaporated to dryness to yield 1.1 mg (5%) of the title compound. MS (m/e): 395.3 (MH$^+$).

Example 3

Cyclopentanecarboxylic acid [6-(4-ethyl-piperazin-1-yl)-pyrimidin-4-yl]-amide

Procedure C:
A mixture of 1.6 g (7.75 mmol) 6-(4-ethyl-piperazin-1-yl)-pyrimidin-4-ylamine (intermediate 4), 2.03 g (9.3 mmol) di-tert-butyl dicarbonate and 1.17 g (11.6 mmol) NEt$_3$ in 30 mL DCM was stirred at 50° C. in a sealed tube for 16 h. After evaporation of all volatiles the residue was purified with flash column chromatography on silica. The combined product fractions were evaporated to dryness to yield [6-(4-ethyl-piperazin-1-yl)-pyrimidin-4-yl]-carbamic acid tert-butyl ester. MS(m/e): 308.4 (MH$^+$). A mixture of 31 mg (0.1 mmol) [6-(4-ethyl-piperazin-1-yl)-pyrimidin-4-yl]-carbamic acid tert-butyl ester, 20 mg (0.15 mmol) cyclopentanecarbonyl chloride and 30 mg (0.3 mmol) NEt$_3$ in 2 mL DCM was shaken at room temperature for 6 h. Subsequently, 3 mL HCl (4N) was added, the mixture was shaken at 50° C. for 4 h and all volatiles removed under reduced pressure. The residue was taken up in methanol/NEt$_3$ and subjected to preparative HPLC purification on reversed phase eluting with a gradient of acetonitrile/water (0.05% triethylamine). The combined product fractions were evaporated to dryness to yield 20 mg (66%) of the title compound as white solid. MS (m/e): 344.1 (MH$^+$).

Example 4

Piperidine-1-carboxylic acid [6-(4-ethyl-piperazin-1-yl)-pyrimidin-4-yl]-amide

Procedure D:
A mixture of 1.6 g (7.75 mmol) 6-(4-ethyl-piperazin-1-yl)-pyrimidin-4-ylamine (intermediate 4), 2.03 g (9.3 mmol) di-tert-butyl dicarbonate and 1.17 g (11.6 mmol) NEt$_3$ in 30 mL DCM was stirred at 50° C. in a sealed tube for 16 h. After evaporation of all volatiles the residue was purified with flash column chromatography on silica. The combined product fractions were evaporated to dryness to yield [6-(4-ethyl-piperazin-1-yl)-pyrimidin-4-yl]-carbamic acid tert-butyl ester. MS(m/e): 308.4 (MH$^+$). A mixture of 28 mg (0.09 mmol) [6-(4-ethyl-piperazin-1-yl)-pyrimidin-4-yl]-carbamic acid tert-butyl ester, 0.18 mL (0.36 mmol) 2M AlMe$_3$ solution in toluene and 30 mg (0.36 mmol) piperidine in 1 mL toluene were heated to 120° C. for 16 h. After removal of all volatiles under reduced pressure the residue was taken up in methanol/NEt$_3$ and subjected to preparative HPLC purification on reversed phase eluting with a gradient of acetonitrile/water (0.05% triethylamine). The combined product fractions were evaporated to dryness to yield 5.3 mg (18%) of the title compound. MS (m/e): 319.1 (MH$^+$).

According to the procedures described for the synthesis of Examples 1, 2, 3 and 4 further pyrimidine derivatives have been synthesized from their respective starting materials and according to the procedure as indicated in table 1. The examples are compiled in table 1 and comprise Example 5 to Example 119.

TABLE 1

| Example | MW | Systematic Name | Starting materials | MW found |
|---|---|---|---|---|
| 5 | 442.01 | 2-(4-chloro-phenyl)-N-[2-(4-cyclopentyl-piperazin-1-yl)-pyrimidin-4-yl]-3-methyl-butyramide | 2-(4-cyclopentyl-piperazin-1-yl)-pyrimidin-4-ylamine (intermediate 1) and 2-(4-chloro-phenyl)-3-methyl-butyryl chloride (commercially available); procedure A | 442.4 |
| 6 | 372.52 | azepane-1-carboxylic acid [2-(4-cyclopentyl-piperazin-1-yl)-pyrimidin-4-yl]-amide | 2-(4-cyclopentyl-piperazin-1-yl)-pyrimidin-4-ylamine (intermediate 2) and azepane (commercially available); procedure B | 373.3 |
| 7 | 317.44 | N-[4-(4-cyclopentyl-piperazin-1-yl)-pyrimidin-2-yl]-butyramide | 4-(4-cyclopentyl-piperazin-1-yl)-pyrimidin-2-ylamine (intermediate 2) and butyryl chloride (commercially available; procedure A | 318.3 |
| 8 | 331.46 | N-[4-(4-cyclopentyl-piperazin-1-yl)-pyrimidin-2-yl]-3-methyl-butyramide | 4-(4-cyclopentyl-piperazin-1-yl)-pyrimidin-2-ylamine (intermediate 2) and 3-methyl-butyryl chloride (commercially available; procedure A | 332.4 |
| 9 | 319.41 | N-[4-(4-cyclopentyl-piperazin-1-yl)-pyrimidin-2-yl]-2-methoxy-acetamide | 4-(4-cyclopentyl-piperazin-1-yl)-pyrimidin-2-ylamine (intermediate 2) and methoxy-acetyl chloride (commercially available; procedure A | 320.3 |
| 10 | 343.47 | cyclopentane carboxylic acid [4-(4-cyclopentyl-piperazin-1-yl)-pyrimidin-2-yl]-amide | 4-(4-cyclopentyl-piperazin-1-yl)-pyrimidin-2-ylamine (intermediate 2) and cyclopentanecarbonyl chloride (commercially available; procedure A | 344.3 |
| 11 | 357.5 | cyclohexane carboxylic acid [4-(4-cyclopentyl-piperazin-1-yl)-pyrimidin-2-yl]-amide | 4-(4-cyclopentyl-piperazin-1-yl)-pyrimidin-2-ylamine (intermediate 2) and cyclohexanecarbonyl chloride (commercially available; procedure A | 358.5 |
| 12 | 381.48 | N-[4-(4-cyclopentyl-piperazin-1-yl)-pyrimidin-2-yl]-4-methoxy-benzamide | 4-(4-cyclopentyl-piperazin-1-yl)-pyrimidin-2-ylamine (intermediate 2) and 4-methoxy-benzoyl chloride (commercially available); procedure A | 382.3 |
| 13 | 442.01 | 2-(4-chloro-phenyl)-N-[4-(4-cyclopentyl-piperazin-1-yl)-pyrimidin-2-yl]-3-methyl-butyramide | 4-(4-cyclopentyl-piperazin-1-yl)-pyrimidin-2-ylamine (intermediate 2) and 2-(4-chloro-phenyl)-3-methyl-butyryl chloride (commercially available); procedure A | 442.5 |
| 14 | 291.4 | N-[4-(4-isopropyl-piperazin-1-yl)-pyrimidin-2-yl]-butyramide | 4-(4-isopropyl-piperazin-1-yl)-pyrimidin-2-ylamine (intermediate 3) and butyryl chloride (commercially available); procedure A | 292.2 |
| 15 | 305.43 | N-[4-(4-isopropyl-piperazin-1-yl)-pyrimidin-2-yl]-3-methyl-butyramide | 4-(4-isopropyl-piperazin-1-yl)-pyrimidin-2-ylamine (intermediate 3) and 3-methyl-butyryl chloride (commercially available); procedure A | 306.3 |
| 16 | 317.44 | cyclopentane carboxylic acid [4-(4-isopropyl-piperazin-1-yl)-pyrimidin-2-yl]-amide | 4-(4-isopropyl-piperazin-1-yl)-pyrimidin-2-ylamine (intermediate 3) and cyclopentanecarbonyl chloride (commercially available); procedure A | 318.2 |
| 17 | 331.46 | cyclohexane carboxylic acid [4-(4-isopropyl-piperazin-1-yl)-pyrimidin-2-yl]-amide | 4-(4-isopropyl-piperazin-1-yl)-pyrimidin-2-ylamine (intermediate 3) and cyclohexanecarbonyl chloride (commercially available); procedure A | 332.4 |
| 18 | 343.41 | 4-fluoro-N-[4-(4-isopropyl-piperazin-1-yl)-pyrimidin-2-yl]- | 4-(4-isopropyl-piperazin-1-yl)-pyrimidin-2-ylamine (intermediate 3) and | 344.3 |

TABLE 1-continued

| Example | MW | Systematic Name | Starting materials | MW found |
|---|---|---|---|---|
| | | benzamide | 4-fluoro-benzoyl chloride (commercially available); procedure A | |
| 19 | 355.44 | N-[4-(4-isopropyl-piperazin-1-yl)-pyrimidin-2-yl]-4-methoxy-benzamide | 4-(4-isopropyl-piperazin-1-yl)-pyrimidin-2-ylamine (intermediate 3) and 4-methoxy-benzoyl chloride (commercially available); procedure A | 356.3 |
| 20 | 317.44 | N-[2-(4-cyclopentyl-piperazin-1-yl)-pyrimidin-4-yl]-butyramide | 2-(4-cyclopentyl-piperazin-1-yl)-pyrimidin-4-ylamine (intermediate 1) and butyryl chloride (commercially available); procedure A | 318.2 |
| 21 | 331.46 | N-[2-(4-cyclopentyl-piperazin-1-yl)-pyrimidin-4-yl]-3-methyl-butyramide | 2-(4-cyclopentyl-piperazin-1-yl)-pyrimidin-4-ylamine (intermediate 1) and 3-methyl-butyryl chloride (commercially available); procedure A | 332.4 |
| 22 | 357.5 | cyclohexane carboxylic acid [2-(4-cyclopentyl-piperazin-1-yl)-pyrimidin-4-yl]-amide | 2-(4-cyclopentyl-piperazin-1-yl)-pyrimidin-4-ylamine (intermediate 1) and cyclohexanecarbonyl chloride (commercially available); procedure A | 358.5 |
| 23 | 369.44 | N-[2-(4-cyclopentyl-piperazin-1-yl)-pyrimidin-4-yl]-4-fluoro-benzamide | 2-(4-cyclopentyl-piperazin-1-yl)-pyrimidin-4-ylamine (intermediate 1) and 4-fluoro-benzoyl chloride (commercially available); procedure A | 370.3 |
| 24 | 329.4 | N-[6-(4-ethyl-piperazin-1-yl)-pyrimidin-4-yl]-4-fluoro-benzamide | 6-(4-ethyl-piperazin-1-yl)-pyrimidin-4-ylamine (intermediate 4) and 4-fluoro-benzoyl chloride (commercially available); procedure C | 330.3 |
| 25 | 317.4 | cyclopentane carboxylic acid [6-(4-isopropyl-piperazin-1-yl)-pyrimidin-4-yl]-amide | 6-(4-isopropyl-piperazin-1-yl)-pyrimidin-4-ylamine (intermediate 4) and cyclopentanecarbonyl chloride (commercially available); procedure C | 318.2 |
| 26 | 305.4 | N-[6-(4-isopropyl-piperazin-1-yl)-pyrimidin-4-yl]-3-methyl-butyramide | 6-(4-isopropyl-piperazin-1-yl)-pyrimidin-4-ylamine (intermediate 4) and 3-methyl-butyryl chloride (commercially available); procedure C | 306.3 |
| 27 | 291.4 | N-[6-(4-isopropyl-piperazin-1-yl)-pyrimidin-4-yl]-butyramide | 6-(4-isopropyl-piperazin-1-yl)-pyrimidin-4-ylamine (intermediate 4) and butyryl chloride (commercially available); procedure C | 292.2 |
| 28 | 343.4 | 4-fluoro-N-[6-(4-isopropyl-piperazin-1-yl)-pyrimidin-4-yl]-benzamide | 6-(4-isopropyl-piperazin-1-yl)-pyrimidin-4-ylamine (intermediate 4) and 4-fluoro-benzoyl chloride (commercially available); procedure C | 344.2 |
| 29 | 319.5 | 2-ethyl-N-[6-(4-isopropyl-piperazin-1-yl)-pyrimidin-4-yl]-butyramide | 6-(4-isopropyl-piperazin-1-yl)-pyrimidin-4-ylamine (intermediate 4) and 3-ethyl-butyryl chloride (commercially available); procedure C | 320.3 |
| 30 | 343.2 | cyclopentane carboxylic acid [6-(4-cyclopentyl-piperazin-1-yl)-pyrimidin-4-yl]-amide | 6-(4-cyclopentyl-piperazin-1-yl)-pyrimidin-4-ylamine (intermediate 6) and cyclopentanecarbonylchloride (commercially available); procedure C | 344.3 |
| 31 | 331.5 | N-[6-(4-cyclopentyl-piperazin-1-yl)-pyrimidin-4-yl]-3- | 6-(4-cyclopentyl-piperazin-1-yl)-pyrimidin-4-ylamine (intermediate 6) and | 332.4 |

TABLE 1-continued

| Example | MW | Systematic Name | Starting materials | MW found |
|---|---|---|---|---|
| | | methyl-butyramide | 3-methyl-butyryl chloride (commercially available); procedure C | |
| 32 | 317.4 | N-[6-(4-cyclopentyl-piperazin-1-yl)-pyrimidin-4-yl]-butyramide | 6-(4-cyclopentyl-piperazin-1-yl)-pyrimidin-4-ylamine (intermediate 6) and butyryl chloride (commercially available); procedure C | 318.2 |
| 33 | 369.4 | N-[6-(4-cyclopentyl-piperazin-1-yl)-pyrimidin-4-yl]-4-fluoro-benzamide | 6-(4-cyclopentyl-piperazin-1-yl)-pyrimidin-4-ylamine (intermediate 6) and 4-fluoro-benzoyl chloride (commercially available); procedure C | 370.3 |
| 34 | 369.4 | N-[6-(4-cyclopentyl-piperazin-1-yl)-pyrimidin-4-yl]-3-fluoro-benzamide | 6-(4-cyclopentyl-piperazin-1-yl)-pyrimidin-4-ylamine (intermediate 6) and 3-fluoro-benzoyl chloride (commercially available); procedure C | 370.3 |
| 35 | 369.4 | N-[6-(4-cyclopentyl-piperazin-1-yl)-pyrimidin-4-yl]-2-fluoro-benzamide | 6-(4-cyclopentyl-piperazin-1-yl)-pyrimidin-4-ylamine (intermediate 6) and 2-fluoro-benzoyl chloride (commercially available); procedure C | 370.3 |
| 36 | 345.5 | N-[6-(4-cyclopentyl-piperazin-1-yl)-pyrimidin-4-yl]-2-ethyl-butyramide | 6-(4-cyclopentyl-piperazin-1-yl)-pyrimidin-4-ylamine (intermediate 6) and 2-ethyl-butyryl chloride (commercially available); procedure C | 346.3 |
| 37 | 345.5 | 2-methyl-pentanoic acid [6-(4-cyclopentyl-piperazin-1-yl)-pyrimidin-4-yl]-amide | 6-(4-cyclopentyl-piperazin-1-yl)-pyrimidin-4-ylamine (intermediate 6) and 2-methylpentanoyl chloride (commercially available); procedure C | 346.3 |
| 38 | 304.4 | pyrrolidine-1-carboxylic acid [6-(4-ethyl-piperazin-1-yl)-pyrimidin-4-yl]-amide | 6-(4-ethyl-piperazin-1-yl)-pyrimidin-4-ylamine (intermediate 2) and pyrrolidine (commercially available); procedure D | 305.2 |
| 39 | 332.5 | 4-methyl-piperidine-1-carboxylic acid [6-(4-ethyl-piperazin-1-yl)-pyrimidin-4-yl]-amide | 6-(4-ethyl-piperazin-1-yl)-pyrimidin-4-ylamine (intermediate 2) and 4-methylpiperidine (commercially available); procedure D | 333.3 |
| 40 | 352.4 | 2,3-dihydro-indole-1-carboxylic acid [6-(4-ethyl-piperazin-1-yl)-pyrimidin-4-yl]-amide | 6-(4-ethyl-piperazin-1-yl)-pyrimidin-4-ylamine (intermediate 2) and 2,3-dihydro-indole (commercially available); procedure D | 353.3 |
| 41 | 332.5 | azepane-1-carboxylic acid [6-(4-ethyl-piperazin-1-yl)-pyrimidin-4-yl]-amide | 6-(4-ethyl-piperazin-1-yl)-pyrimidin-4-ylamine (intermediate 2) and azepane (commercially available); procedure D | 333.2 |
| 42 | 318.4 | 2-methyl-pyrrolidine-1-carboxylic acid [6-(4-ethyl-piperazin-1-yl)-pyrimidin-4-yl]-amide | 6-(4-ethyl-piperazin-1-yl)-pyrimidin-4-ylamine (intermediate 2) and 2-methyl-pyrrolidine (commercially available); procedure D | 319.2 |
| 43 | 332.5 | 3-methyl-piperidine-1-carboxylic acid [6-(4-ethyl-piperazin-1-yl)-pyrimidin-4-yl]-amide | 6-(4-ethyl-piperazin-1-yl)-pyrimidin-4-ylamine (intermediate 2) and 3-methyl-piperidine (commercially available); procedure D | 333.3 |
| 44 | 372.5 | octahydro-isoquinoline-2-carboxylic acid [6-(4-ethyl-piperazin-1-yl)-pyrimidin-4-yl]-amide | 6-(4-ethyl-piperazin-1-yl)-pyrimidin-4-ylamine (intermediate 2) and octahydro-isoquinoline (commercially available); procedure D | 373.2 |

TABLE 1-continued

| Example | MW | Systematic Name | Starting materials | MW found |
|---|---|---|---|---|
| 45 | 352.4 | 1,3-dihydro-isoindole-2-carboxylic acid [6-(4-ethyl-piperazin-1-yl)-pyrimidin-4-yl]-amide | 6-(4-ethyl-piperazin-1-yl)-pyrimidin-4-ylamine (intermediate 2) and 1,3-dihydro-isoindole (commercially available); procedure D | 353.3 |
| 46 | 304.4 | 1-cyclopropylmethyl-3-[6-(4-ethyl-piperazin-1-yl)-pyrimidin-4-yl]-urea | 6-(4-ethyl-piperazin-1-yl)-pyrimidin-4-ylamine (intermediate 2) and cyclopropylmethylamine (commercially available); procedure D | 305.2 |
| 47 | 308.4 | 1-[6-(4-ethyl-piperazin-1-yl)-pyrimidin-4-yl]-3-(2-methoxy-ethyl)-urea | 6-(4-ethyl-piperazin-1-yl)-pyrimidin-4-ylamine (intermediate 2) and 2-methoxy-ethylamine (commercially available); procedure D | 309.2 |
| 48 | 320.4 | 1-(1,2-dimethyl-propyl)-3-[6-(4-ethyl-piperazin-1-yl)-pyrimidin-4-yl]-urea | 6-(4-ethyl-piperazin-1-yl)-pyrimidin-4-ylamine (intermediate 2) and 1,2-dimethyl-propylamine (commercially available); procedure D | 321.2 |
| 49 | 318.4 | 1-cyclopentyl-3-[6-(4-ethyl-piperazin-1-yl)-pyrimidin-4-yl]-urea | 6-(4-ethyl-piperazin-1-yl)-pyrimidin-4-ylamine (intermediate 2) and cyclopentylamine (commercially available); procedure D | 319.2 |
| 50 | 372.4 | 1-[6-(4-ethyl-piperazin-1-yl)-pyrimidin-4-yl]-3-[1-(4-fluoro-phenyl)-ethyl]-urea | 6-(4-ethyl-piperazin-1-yl)-pyrimidin-4-ylamine (intermediate 2) and 1-(4-fluoro-phenyl)-ethylamine (commercially available); procedure D | 373.2 |
| 51 | 366.5 | 1-[6-(4-ethyl-piperazin-1-yl)-pyrimidin-4-yl]-3-indan-1-yl-urea | 6-(4-ethyl-piperazin-1-yl)-pyrimidin-4-ylamine (intermediate 2) and indan-1-ylamine (commercially available); procedure D | 367.2 |
| 52 | 358.4 | 1-[6-(4-ethyl-piperazin-1-yl)-pyrimidin-4-yl]-3-(4-fluoro-benzyl)-urea | 6-(4-ethyl-piperazin-1-yl)-pyrimidin-4-ylamine (intermediate 2) and 4-fluorobenzylamine (commercially available); procedure D | 359.3 |
| 53 | 344.4 | 1-[6-(4-ethyl-piperazin-1-yl)-pyrimidin-4-yl]-3-(4-fluoro-phenyl)-urea | 6-(4-ethyl-piperazin-1-yl)-pyrimidin-4-ylamine (intermediate 2) and 4-fluoroaniline (commercially available); procedure D | 345.1 |
| 54 | 332.5 | piperidine-1-carboxylic acid [6-(4-isopropyl-piperazin-1-yl)-pyrimidin-4-yl]-amide | 6-(4-isopropyl-piperazin-1-yl)-pyrimidin-4-ylamine (intermediate 5) and piperidine (commercially available); procedure D | 333.3 |
| 55 | 334.4 | morpholine-4-carboxylic acid [6-(4-isopropyl-piperazin-1-yl)-pyrimidin-4-yl]-amide | 6-(4-isopropyl-piperazin-1-yl)-pyrimidin-4-ylamine (intermediate 5) and morpholine (commercially available); procedure D | 335.3 |
| 56 | 318.4 | pyrrolidine-1-carboxylic acid [6-(4-isopropyl-piperazin-1-yl)-pyrimidin-4-yl]-amide | 6-(4-isopropyl-piperazin-1-yl)-pyrimidin-4-ylamine (intermediate 5) and pyrrolidine (commercially available); procedure D | 319.1 |
| 57 | 346.5 | 4-methyl-piperidine-1-carboxylic acid [6-(4-isopropyl-piperazin-1-yl)-pyrimidin-4-yl]-amide | 6-(4-isopropyl-piperazin-1-yl)-pyrimidin-4-ylamine (intermediate 5) and 4-methylpiperidine (commercially available); procedure D | 347.3 |

TABLE 1-continued

| Example | MW | Systematic Name | Starting materials | MW found |
|---|---|---|---|---|
| 58 | 366.5 | 2,3-dihydro-indole-1-carboxylic acid [6-(4-isopropyl-piperazin-1-yl)-pyrimidin-4-yl]-amide | 6-(4-isopropyl-piperazin-1-yl)-pyrimidin-4-ylamine (intermediate 5) and indan-1-ylamine (commercially available); procedure D | 367.2 |
| 59 | 346.5 | azepane-1-carboxylic acid [6-(4-isopropyl-piperazin-1-yl)-pyrimidin-4-yl]-amide | 6-(4-isopropyl-piperazin-1-yl)-pyrimidin-4-ylamine (intermediate 5) and azepane (commercially available); procedure D | 347.3 |
| 60 | 332.5 | 2-methyl-pyrrolidine-1-carboxylic acid [6-(4-isopropyl-piperazin-1-yl)-pyrimidin-4-yl]-amide | 6-(4-isopropyl-piperazin-1-yl)-pyrimidin-4-ylamine (intermediate 5) and 2-methylpyrrolidine (commercially available); procedure D | 333.3 |
| 61 | 346.5 | 3-methyl-piperidine-1-carboxylic acid [6-(4-isopropyl-piperazin-1-yl)-pyrimidin-4-yl]-amide | 6-(4-isopropyl-piperazin-1-yl)-pyrimidin-4-ylamine (intermediate 5) and 3-methylpiperidine (commercially available); procedure D | 347.3 |
| 62 | 386.5 | octahydro-isoquinoline-2-carboxylic acid [6-(4-isopropyl-piperazin-1-yl)-pyrimidin-4-yl]-amide | 6-(4-isopropyl-piperazin-1-yl)-pyrimidin-4-ylamine (intermediate 5) and octahydro-isoquinoline (commercially available); procedure D | 387.3 |
| 63 | 366.5 | 1,3-dihydro-isoindole-2-carboxylic acid [6-(4-isopropyl-piperazin-1-yl)-pyrimidin-4-yl]-amide | 6-(4-isopropyl-piperazin-1-yl)-pyrimidin-4-ylamine (intermediate 5) and 1,3-dihydroisoindole (commercially available); procedure D | 367.2 |
| 64 | 318.4 | 1-cyclopropylmethyl-3-[6-(4-isopropyl-piperazin-1-yl)-pyrimidin-4-yl]-urea | 6-(4-isopropyl-piperazin-1-yl)-pyrimidin-4-ylamine (intermediate 5) and cyclopropylmethylamine (commercially available); procedure D | 319.2 |
| 65 | 306.4 | 1-[6-(4-isopropyl-piperazin-1-yl)-pyrimidin-4-yl]-3-propyl-urea | 6-(4-isopropyl-piperazin-1-yl)-pyrimidin-4-ylamine (intermediate 5) and propylamine (commercially available); procedure D | 307.2 |
| 66 | 322.4 | 1-[6-(4-isopropyl-piperazin-1-yl)-pyrimidin-4-yl]-3-(2-methoxy-ethyl)-urea | 6-(4-isopropyl-piperazin-1-yl)-pyrimidin-4-ylamine (intermediate 5) and 2-methoxyethylamine (commercially available); procedure D | 323.2 |
| 67 | 334.5 | 1-(1,2-dimethyl-propyl)-3-[6-(4-isopropyl-piperazin-1-yl)-pyrimidin-4-yl]-urea | 6-(4-isopropyl-piperazin-1-yl)-pyrimidin-4-ylamine (intermediate 5) and 1,2-dimethyl-propyl amine (commercially available); procedure D | 335.3 |
| 68 | 332.5 | 1-cyclopentyl-3-[6-(4-isopropyl-piperazin-1-yl)-pyrimidin-4-yl]-urea | 6-(4-isopropyl-piperazin-1-yl)-pyrimidin-4-ylamine (intermediate 5) and cyclopentylamine (commercially available); procedure D | 333.3 |
| 69 | 386.5 | 1-[1-(4-fluoro-phenyl)-ethyl]-3-[6-(4-isopropyl-piperazin-1-yl)-pyrimidin-4-yl]-urea | 6-(4-isopropyl-piperazin-1-yl)-pyrimidin-4-ylamine (intermediate 5) and 1-(4-fluoro-phenyl)-ethylamine (commercially available); procedure D | 387.3 |
| 70 | 380.5 | 1-indan-1-yl-3-[6-(4-isopropyl-piperazin-1-yl)-pyrimidin-4-yl]-urea | 6-(4-isopropyl-piperazin-1-yl)-pyrimidin-4-ylamine (intermediate 5) and indan-1-ylamine (commercially available); procedure D | 381.3 |
| 71 | 370.5 | 1-[6-(4-isopropyl-piperazin-1-yl)- | 6-(4-isopropyl-piperazin-1-yl)-pyrimidin-4-ylamine | 371.1 |

TABLE 1-continued

| Example | MW | Systematic Name | Starting materials | MW found |
|---|---|---|---|---|
| | | pyrimidin-4-yl]-3-(2-methoxy-phenyl)-urea | (intermediate 5) and 2-methoxyaniline (commercially available); procedure D | |
| 72 | 372.4 | 1-(4-fluoro-benzyl)-3-[6-(4-isopropyl-piperazin-1-yl)-pyrimidin-4-yl]-urea | 6-(4-isopropyl-piperazin-1-yl)-pyrimidin-4-ylamine (intermediate 5) and 4-fluorobenzylamine (commercially available); procedure D | 373.2 |
| 73 | 358.4 | 1-(4-fluoro-phenyl)-3-[6-(4-isopropyl-piperazin-1-yl)-pyrimidin-4-yl]-urea | 6-(4-isopropyl-piperazin-1-yl)-pyrimidin-4-ylamine (intermediate 5) and 4-fluoroaniline (commercially available); procedure D | 359.3 |
| 74 | 358.5 | 2-methyl-pyrrolidine-1-carboxylic acid [6-(4-cyclopentyl-piperazin-1-yl)-pyrimidin-4-yl]-amide | 6-(4-cyclopentyl-piperazin-1-yl)-pyrimidin-4-ylamine (intermediate 6) and 2-methylpyrrolidine (commercially available); procedure D | 359.3 |
| 75 | 372.5 | 3-methyl-piperidine-1-carboxylic acid [6-(4-cyclopentyl-piperazin-1-yl)-pyrimidin-4-yl]-amide | 6-(4-cyclopentyl-piperazin-1-yl)-pyrimidin-4-ylamine (intermediate 6) and 3-methylpiperidine (commercially available); procedure D | 373.3 |
| 76 | 428.6 | 1-cyclohexyl-3-[6-(4-cyclohexyl-piperazin-1-yl)-pyrimidin-4-yl]-1-isopropyl-urea | 6-(4-cyclohexyl-piperazin-1-yl)-pyrimidin-4-ylamine (intermediate 7) and cyclohexyl-isopropylamine (commercially available); procedure D | 429.5 |
| 77 | 372.5 | piperidine-1-carboxylic acid [6-(4-cyclohexyl-piperazin-1-yl)-pyrimidin-4-yl]-amide | 6-(4-cyclohexyl-piperazin-1-yl)-pyrimidin-4-ylamine (intermediate 7) and piperidine (commercially available); procedure D | 373.3 |
| 78 | 358.5 | pyrrolidine-1-carboxylic acid [6-(4-cyclohexyl-piperazin-1-yl)-pyrimidin-4-yl]-amide | 6-(4-cyclohexyl-piperazin-1-yl)-pyrimidin-4-ylamine (intermediate 7) and pyrrolidine (commercially available); procedure D | 359.4 |
| 79 | 374.5 | morpholine-4-carboxylic acid [6-(4-cyclohexyl-piperazin-1-yl)-pyrimidin-4-yl]-amide | 6-(4-cyclohexyl-piperazin-1-yl)-pyrimidin-4-ylamine (intermediate 7) and morpholine (commercially available); procedure D | 375.4 |
| 80 | 386.5 | 3-methyl-piperidine-1-carboxylic acid [6-(4-cyclohexyl-piperazin-1-yl)-pyrimidin-4-yl]-amide | 6-(4-cyclohexyl-piperazin-1-yl)-pyrimidin-4-ylamine (intermediate 7) and 3-methylpiperidine (commercially available); procedure D | 387.3 |
| 81 | 386.5 | 1-cyclohexyl-3-[6-(4-cyclohexyl-piperazin-1-yl)-pyrimidin-4-yl]-urea | 6-(4-cyclohexyl-piperazin-1-yl)-pyrimidin-4-ylamine (intermediate 7) and cyclohexylamine (commercially available); procedure D | 387.1 |
| 82 | 386.5 | azepane-1-carboxylic acid [6-(4-cyclohexyl-piperazin-1-yl)-pyrimidin-4-yl]-amide | 6-(4-cyclohexyl-piperazin-1-yl)-pyrimidin-4-ylamine (intermediate 7) and azepane (commercially available); procedure D | 387.3 |
| 83 | 386.5 | 2-methyl-piperidine-1-carboxylic acid [6-(4-cyclohexyl-piperazin-1-yl)-pyrimidin-4-yl]-amide | 6-(4-cyclohexyl-piperazin-1-yl)-pyrimidin-4-ylamine (intermediate 7) and 2-methyl-piperidine (commercially available); procedure D | 387.3 |
| 84 | 372.5 | 1-[6-(4-cyclohexyl-piperazin-1-yl)-pyrimidin-4-yl]-3-cyclopentyl-urea | 6-(4-cyclohexyl-piperazin-1-yl)-pyrimidin-4-ylamine (intermediate 7) and cyclopentylamine (commercially available); procedure D | 373.3 |

TABLE 1-continued

| Example | MW | Systematic Name | Starting materials | MW found |
|---|---|---|---|---|
| 85 | 400.6 | 2-isopropyl-pyrrolidine-1-carboxylic acid [6-(4-cyclohexyl-piperazin-1-yl)-pyrimidin-4-yl]-amide | 6-(4-cyclohexyl-piperazin-1-yl)-pyrimidin-4-ylamine (intermediate 7) and 2-isopropyl-pyrrolidine (commercially available); procedure D | 401.4 |
| 86 | 386.5 | 4-methyl-piperidine-1-carboxylic acid [6-(4-cyclohexyl-piperazin-1-yl)-pyrimidin-4-yl]-amide | 6-(4-cyclohexyl-piperazin-1-yl)-pyrimidin-4-ylamine (intermediate 7) and 4-methyl-piperidine (commercially available); procedure D | 387.3 |
| 87 | 426.6 | octahydro-quinoline-1-carboxylic acid [6-(4-cyclohexyl-piperazin-1-yl)-pyrimidin-4-yl]-amide | 6-(4-cyclohexyl-piperazin-1-yl)-pyrimidin-4-ylamine (intermediate 7) and octahydro-quinoline (commercially available); procedure D | 427.4 |
| 88 | 374.5 | 3-hydroxy-pyrrolidine-1-carboxylic acid [6-(4-cyclohexyl-piperazin-1-yl)-pyrimidin-4-yl]-amide | 6-(4-cyclohexyl-piperazin-1-yl)-pyrimidin-4-ylamine (intermediate 7) and 3-hydroxy-pyrrolidine (commercially available); procedure D | 375.3 |
| 89 | 408.5 | 4,4-difluoro-piperidine-1-carboxylic acid [6-(4-cyclohexyl-piperazin-1-yl)-pyrimidin-4-yl]-amide | 6-(4-cyclohexyl-piperazin-1-yl)-pyrimidin-4-ylamine (intermediate 7) and 4,4-difluoro-piperidine (commercially available); procedure D | 410.2 |
| 90 | 408.5 | 3,3-difluoro-piperidine-1-carboxylic acid [6-(4-cyclohexyl-piperazin-1-yl)-pyrimidin-4-yl]-amide | 6-(4-cyclohexyl-piperazin-1-yl)-pyrimidin-4-ylamine (intermediate 7) and 3,3-difluoro-piperidine (commercially available); procedure D | 409.4 |
| 91 | 356.5 | 2,5-dihydro-pyrrole-1-carboxylic acid [6-(4-cyclohexyl-piperazin-1-yl)-pyrimidin-4-yl]-amide | 6-(4-cyclohexyl-piperazin-1-yl)-pyrimidin-4-ylamine (intermediate 7) and 2,5-dihydro-pyrrole (commercially available); procedure D | 357.3 |
| 92 | 388.5 | 3-hydroxy-piperidine-1-carboxylic acid [6-(4-cyclohexyl-piperazin-1-yl)-pyrimidin-4-yl]-amide | 6-(4-cyclohexyl-piperazin-1-yl)-pyrimidin-4-ylamine (intermediate 7) and 3-hydroxy-piperidine (commercially available); procedure D | 389.4 |
| 93 | 400.6 | 3,5-Dimethyl-piperidine-1-carboxylic acid [6-(4-cyclohexyl-piperazin-1-yl)-pyrimidin-4-yl]-amide | 6-(4-cyclohexyl-piperazin-1-yl)-pyrimidin-4-ylamine (intermediate 7) and 3,5-dimethyl-piperidine (commercially available); procedure D | 401.4 |
| 94 | 440.5 | 4-trifluoromethyl-piperidine-1-carboxylic acid [6-(4-cyclohexyl-piperazin-1-yl)-pyrimidin-4-yl]-amide | 6-(4-cyclohexyl-piperazin-1-yl)-pyrimidin-4-ylamine (intermediate 7) and 4-trifluoromethyl-piperidine (commercially available); procedure D | 441.4 |
| 95 | 360.5 | 3-[6-(4-cyclohexyl-piperazin-1-yl)-pyrimidin-4-yl]-1,1-diethyl-urea | 6-(4-cyclohexyl-piperazin-1-yl)-pyrimidin-4-ylamine (intermediate 7) and diethylamine (commercially available); procedure D | 361.4 |
| 96 | 390.5 | 4-fluoro-piperidine-1-carboxylic acid [6-(4-cyclohexyl-piperazin-1-yl)-pyrimidin-4-yl]-amide | 6-(4-cyclohexyl-piperazin-1-yl)-pyrimidin-4-ylamine (intermediate 7) and 4-fluoro-piperidine (commercially available); procedure D | 391.2 |
| 97 | 414.6 | 1-cyclohexyl-3-[6-(4-cyclopentyl-piperazin-1-yl)-pyrimidin-4-yl]-1-isopropyl-urea | 6-(4-cyclopentyl-piperazin-1-yl)-pyrimidin-4-ylamine (intermediate 6) and cyclohexyl-isopropylamine (commercially available); procedure D | 415.5 |

TABLE 1-continued

| Example | MW | Systematic Name | Starting materials | MW found |
|---|---|---|---|---|
| 98 | 358.5 | piperidine-1-carboxylic acid [6-(4-cyclopentyl-piperazin-1-yl)-pyrimidin-4-yl]-amide | 6-(4-cyclopentyl-piperazin-1-yl)-pyrimidin-4-ylamine (intermediate 6) and piperidine (commercially available); procedure D | 359.3 |
| 99 | 344.5 | pyrrolidine-1-carboxylic acid [6-(4-cyclopentyl-piperazin-1-yl)-pyrimidin-4-yl]-amide | 6-(4-cyclopentyl-piperazin-1-yl)-pyrimidin-4-ylamine (intermediate 6) and pyrrolidine (commercially available); procedure D | 345.2 |
| 100 | 360.5 | morpholine-4-carboxylic acid [6-(4-cyclopentyl-piperazin-1-yl)-pyrimidin-4-yl]-amide | 6-(4-cyclopentyl-piperazin-1-yl)-pyrimidin-4-ylamine (intermediate 6) and morpholine (commercially available); procedure D | 361.1 |
| 101 | 392.5 | 1,3-dihydro-isoindole-2-carboxylic acid [6-(4-cyclopentyl-piperazin-1-yl)-pyrimidin-4-yl]-amide | 6-(4-cyclopentyl-piperazin-1-yl)-pyrimidin-4-ylamine (intermediate 6) and 1,3-dihydro-isoindole (commercially available); procedure D | 393.1 |
| 102 | 372.5 | 1-cyclohexyl-3-[6-(4-cyclopentyl-piperazin-1-yl)-pyrimidin-4-yl]-urea | 6-(4-cyclopentyl-piperazin-1-yl)-pyrimidin-4-ylamine (intermediate 6) and cyclohexylamine (commercially available); procedure D | 373.3 |
| 103 | 372.5 | azepane-1-carboxylic acid [6-(4-cyclopentyl-piperazin-1-yl)-pyrimidin-4-yl]-amide | 6-(4-cyclopentyl-piperazin-1-yl)-pyrimidin-4-ylamine (intermediate 6) and azepane (commercially available); procedure D | 373.3 |
| 104 | 372.5 | 2-methyl-piperidine-1-carboxylic acid [6-(4-cyclopentyl-piperazin-1-yl)-pyrimidin-4-yl]-amide | 6-(4-cyclopentyl-piperazin-1-yl)-pyrimidin-4-ylamine (intermediate 6) and 2-methylpiperidine (commercially available); procedure D | 373.3 |
| 105 | 358.5 | 1-cyclopentyl-3-[6-(4-cyclopentyl-piperazin-1-yl)-pyrimidin-4-yl]-urea | 6-(4-cyclopentyl-piperazin-1-yl)-pyrimidin-4-ylamine (intermediate 6) and cyclopentylamine (commercially available); procedure D | 359.4 |
| 106 | 386.5 | 2-isopropyl-pyrrolidine-1-carboxylic acid [6-(4-cyclopentyl-piperazin-1-yl)-pyrimidin-4-yl]-amide | 6-(4-cyclopentyl-piperazin-1-yl)-pyrimidin-4-ylamine (intermediate 6) and 2-isopropyl-pyrrolidine (commercially available); procedure D | 387.3 |
| 107 | 372.5 | 4-methyl-piperidine-1-carboxylic acid [6-(4-cyclopentyl-piperazin-1-yl)-pyrimidin-4-yl]-amide | 6-(4-cyclopentyl-piperazin-1-yl)-pyrimidin-4-ylamine (intermediate 6) and 4-methylpiperidine (commercially available); procedure D | 373.3 |
| 108 | 412.6 | octahydro-quinoline-1-carboxylic acid [6-(4-cyclopentyl-piperazin-1-yl)-pyrimidin-4-yl]-amide | 6-(4-cyclopentyl-piperazin-1-yl)-pyrimidin-4-ylamine (intermediate 6) and octahydro-quinoline (commercially available); procedure D | 413.4 |
| 109 | 360.5 | 3-hydroxy-pyrrolidine-1-carboxylic acid [6-(4-cyclopentyl-piperazin-1-yl)-pyrimidin-4-yl]-amide | 6-(4-cyclopentyl-piperazin-1-yl)-pyrimidin-4-ylamine (intermediate 6) and 3-hydroxy-pyrrolidine (commercially available); procedure D | 361.3 |
| 110 | 394.5 | 4,4-difluoro-piperidine-1-carboxylic acid [6-(4-cyclopentyl-piperazin-1-yl)-pyrimidin-4-yl]-amide | 6-(4-cyclopentyl-piperazin-1-yl)-pyrimidin-4-ylamine (intermediate 6) and 4,4-difluoro-piperidine (commercially available); procedure D | 395.3 |
| 111 | 394.5 | 3,3-difluoro-piperidine-1-carboxylic acid [6-(4-cyclopentyl-piperazin- | 6-(4-cyclopentyl-piperazin-1-yl)-pyrimidin-4-ylamine (intermediate 6) and 3,3-difluoro-piperidine | 395.3 |

TABLE 1-continued

| Example | MW | Systematic Name | Starting materials | MW found |
|---|---|---|---|---|
| | | 1-yl)-pyrimidin-4-yl]-amide | (commercially available); procedure D | |
| 112 | 388.5 | 4-methoxy-piperidine-1-carboxylic acid [6-(4-cyclopentyl-piperazin-1-yl)-pyrimidin-4-yl]-amide | 6-(4-cyclopentyl-piperazin-1-yl)-pyrimidin-4-ylamine (intermediate 6) and 4-methoxy-piperidine (commercially available); procedure D | 389.3 |
| 113 | 342.4 | 2,5-dihydro-pyrrole-1-carboxylic acid [6-(4-cyclopentyl-piperazin-1-yl)-pyrimidin-4-yl]-amide | 6-(4-cyclopentyl-piperazin-1-yl)-pyrimidin-4-ylamine (intermediate 6) and 2,5-dihydro-pyrrole (commercially available); procedure D | 343.3 |
| 114 | 374.5 | 3-hydroxy-piperidine-1-carboxylic acid [6-(4-cyclopentyl-piperazin-1-yl)-pyrimidin-4-yl]-amide | 6-(4-cyclopentyl-piperazin-1-yl)-pyrimidin-4-ylamine (intermediate 6) and 3-hydroxy-piperidine (commercially available); procedure D | 375.4 |
| 115 | 386.5 | 3,5-dimethyl-piperidine-1-carboxylic acid [6-(4-cyclopentyl-piperazin-1-yl)-pyrimidin-4-yl]-amide | 6-(4-cyclopentyl-piperazin-1-yl)-pyrimidin-4-ylamine (intermediate 6) and 3,5-dimethyl-piperidine (commercially available); procedure D | 387.3 |
| 116 | 426.5 | 4-trifluoromethyl-piperidine-1-carboxylic acid [6-(4-cyclopentyl-piperazin-1-yl)-pyrimidin-4-yl]-amide | 6-(4-cyclopentyl-piperazin-1-yl)-pyrimidin-4-ylamine (intermediate 6) and 4-trifluoromethyl-piperidine (commercially available); procedure D | 427.3 |
| 117 | 332.5 | 1-[6-(4-cyclopentyl-piperazin-1-yl)-pyrimidin-4-yl]-3-propyl-urea | 6-(4-cyclopentyl-piperazin-1-yl)-pyrimidin-4-ylamine (intermediate 6) and propylamine (commercially available); procedure D | 333.4 |
| 118 | 346.5 | 3-[6-(4-cyclopentyl-piperazin-1-yl)-pyrimidin-4-yl]-1,1-diethyl-urea | 6-(4-cyclopentyl-piperazin-1-yl)-pyrimidin-4-ylamine (intermediate 6) and diethylamine (commercially available); procedure D | 347.3 |
| 119 | 376.5 | 4-fluoro-piperidine-1-carboxylic acid [6-(4-cyclopentyl-piperazin-1-yl)-pyrimidin-4-yl]-amide | 6-(4-cyclopentyl-piperazin-1-yl)-pyrimidin-4-ylamine (intermediate 6) and 4-fluoro-piperidine (commercially available); procedure D | 377.4 |

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |

-continued

| Ingredients | Per capsule |
|---|---|
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Gelatine | 150.0 mg |
| Phenol | 4.7 mg |
| Sodium carbonate | to obtain a final pH of 7 |
| Water for injection solutions | ad 1.0 ml |

Example D

Soft gelatin capsules containing the following ingredients can be manufactured in a conventional manner:

| Capsule contents | |
|---|---|
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 (sorbitol) | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula (I) | 50.0 mg |
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

Unless stated to the contrary, all compounds in the examples were prepared and characterized as described. All ranges recited herein encompass all combinations and subcombinations included within that range limit. All patents and publications cited herein are hereby incorporated by reference in their entirety.

The invention claimed is:

1. A compound of formula I:

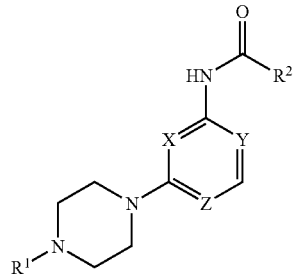

or a pharmaceutically acceptable salt thereof, wherein:
(a) $R^1$ is lower alkyl or $C_3$-$C_7$-cycloalkyl;
(b) X, Y, and Z are defined in one of three groups selected from the group consisting of:
  (1) wherein X is N, Y is C and Z is N,
  (2) wherein X is N, Y is N and Z is C, and
  (3) wherein X is C, Y is N and Z is N;
(c) $R^2$ is selected from the group consisting of:
  (1) lower alkyl,
  (2) lower halogenalkyl,
  (3) lower hydroxyalkyl,
  (4) lower alkoxyalkyl,
  (5) $C_3$-$C_7$-cycloalkyl or $C_3$-$C_7$-cycloalkyl substituted by phenyl or lower alkyl,
  (6) lower $C_3$-$C_7$-cycloalkylalkyl,
  (7) phenyl mono- or disubstituted by lower alkyl, lower alkoxy, halogen or lower halogenalkyl,
  (8) lower phenylalkyl wherein the phenyl ring is mono- or disubstituted by lower alkyl, lower alkoxy, halogen or lower halogenalkyl, and
  (9) —$NR^3R^4$;
(d) $R^3$ is hydrogen or lower alkyl, and $R^4$ is selected from the group consisting of:
  (1) lower alkyl,
  (2) lower alkoxyalkyl,
  (3) $C_3$-$C_7$-cycloalkyl or $C_3$-$C_7$-cycloalkyl substituted by phenyl,
  (4) lower $C_3$-$C_7$-cycloalkylalkyl,
  (5) unsubstituted phenyl or phenyl mono- or disubstituted by lower alkyl, lower alkoxy, halogen or lower halogenalkyl,
  (6) lower phenylalkyl wherein the phenyl ring is unsubstituted or mono- or disubstituted by lower alkyl, lower alkoxy, halogen or lower halogenalkyl, and
  (7) indanyl; or alternatively,
$R^3$ and $R^4$ together with the nitrogen atom to which they are attached form a 4-, 5-, 6- or 7-membered saturated or partly unsaturated heterocyclic ring optionally containing a further heteroatom of nitrogen, oxygen or sulfur; wherein said heterocyclic ring is optionally substituted by one, two or three substituents independently selected from the group consisting of lower alkyl, lower alkoxy, hydroxy, halogen and halogenalkyl; or said heterocyclic ring is optionally condensed with a phenyl or cyclohexyl ring, wherein said phenyl or cyclohexyl ring is optionally substituted by one, two or three substituents independently selected from the group consisting of lower alkyl, lower alkoxy, hydroxy, halogen and halogenalkyl.

2. A compound of claim 1 wherein $R^1$ is $C_3$-$C_7$-cycloalkyl.

3. A compound of claim 1 wherein $R^1$ is ethyl or isopropyl.

4. A compound of claim 1 wherein $R^2$ is —$NR^3R^4$.

5. A compound of claim 1 wherein $R^3$ is hydrogen or lower alkyl and $R^4$ is selected from the group consisting of
   (1) lower alkyl,
   (2) lower alkoxyalkyl,
   (3) $C_3$-$C_7$-cycloalkyl or $C_3$-$C_7$-cycloalkyl substituted by phenyl,
   (4) lower $C_3$-$C_7$-cycloalkylalkyl,
   (5) unsubstituted phenyl or phenyl mono- or disubstituted by lower alkyl, lower alkoxy, halogen or lower halogenalkyl,
   (6) lower phenylalkyl wherein the phenyl ring is unsubstituted or mono- or disubstituted by lower alkyl, lower alkoxy, halogen or lower halogenalkyl, and
   (7) indanyl.

6. A compound of claim 1 wherein $R^3$ and $R^4$ together with the nitrogen atom to which they are attached form a 4-, 5-, 6- or 7-membered saturated or partly unsaturated heterocyclic ring optionally containing a further heteroatom of nitrogen, oxygen or sulfur; wherein said heterocyclic ring is optionally substituted by one, two or three substituents independently selected from the group consisting of lower alkyl, lower alkoxy, hydroxy, halogen and halogenalkyl; or said heterocyclic ring is optionally condensed with a phenyl or cyclohexyl ring, wherein said phenyl or cyclohexyl ring is optionally substituted by one, two or three substituents independently selected from the group consisting of lower alkyl, lower alkoxy, hydroxy, halogen, and halogenalkyl.

7. A compound of claim 1 wherein $R^3$ and $R^4$ together with the nitrogen atom to which they are attached form a heterocyclic ring selected from the group consisting of azetidine, pyrrolidine, 2,5-dihydropyrrole, morpholine, piperazine, thiomorpholine, piperidine and azepane; wherein said heterocyclic ring is optionally substituted by one, two or three substituents independently selected from the group consisting of lower alkyl, lower alkoxy, hydroxy, halogen, and halogenalkyl; or said heterocyclic ring is optionally condensed with a phenyl or cyclohexyl ring, wherein said phenyl or cyclohexyl ring is optionally substituted by one, two or three substituents independently selected from the group consisting of lower alkyl, lower alkoxy, hydroxy, halogen, and halogenalkyl.

8. A compound of claim 1 wherein $R^3$ and $R^4$ together with the nitrogen atom to which they are attached form a heterocyclic ring selected from the group consisting of piperidine, pyrrolidine, 2,5-dihydropyrrole, azepane, 2,3-dihydroindole, 1,3-dihydroisoindole, octahydroquinoline, octahydroisoquinoline and morpholine, wherein said heterocyclic ring is optionally substituted by one, two or three substituents independently selected from the group consisting of lower alkyl, lower alkoxy, hydroxy, halogen, and halogenalkyl.

9. A compound of claim 1 wherein $R^3$ and $R^4$ together with the nitrogen atom to which they are attached form a heterocyclic ring selected from the group consisting of piperidine, 2-methylpiperidine, 3-methylpiperidine, 4-methylpiperidine, 3,5-dimethylpiperidine, 4-fluoropiperidine, 4-trifluoromethyl-piperidine, 3-hydroxypiperidine, 3,3-difluoropiperidine, 4,4-difluoropiperidine, pyrrolidine, 2-methylpyrrolidine, 2-isopropylpyrrolidine, 3-hydroxypyrrolidine, 2,5-dihydropyrrole, azepane, 2,3-dihydroindole, 1,3-dihydroisoindole, octahydroquinoline, octahydroisoquinoline, and morpholine.

10. A compound of claim 1 wherein $R^2$ is selected from the group consisting of:
    (1) lower alkyl,
    (2) lower halogenalkyl,
    (3) lower hydroxyalkyl,
    (4) lower alkoxyalkyl,
    (5) $C_3$-$C_7$-cycloalkyl or $C_3$-$C_7$-cycloalkyl substituted by phenyl or lower alkyl,
    (6) lower $C_3$-$C_7$-cycloalkylalkyl,
    (7) phenyl mono- or disubstituted by lower alkyl, lower alkoxy, halogen or lower halogenalkyl, and
    (8) lower phenylalkyl wherein the phenyl ring is mono- or disubstituted by lower alkyl, lower alkoxy, halogen or lower halogenalkyl.

11. A compound of claim 1 wherein $R^2$ is selected from the group consisting of:
    (1) lower alkyl,
    (2) lower alkoxyalkyl,
    (3) $C_3$-$C_7$-cycloalkyl or $C_3$-$C_7$-cycloalkyl substituted by phenyl or lower alkyl,
    (4) phenyl mono- or disubstituted by lower alkyl, lower alkoxy, halogen or lower halogenalkyl, and
    (5) lower phenylalkyl wherein the phenyl ring is mono- or disubstituted by lower alkyl, lower alkoxy, halogen or lower halogenalkyl.

12. A compound of claim 1 wherein $R^2$ is selected from the group consisting of:
    (1) lower alkyl,
    (2) lower alkoxyalkyl,
    (3) $C_3$-$C_7$-cycloalkyl, and
    (4) lower phenylalkyl wherein the phenyl ring is mono- or disubstituted by lower alkyl, lower alkoxy, halogen or lower halogenalkyl.

13. A compound of claim 1 wherein X is N, Y is C and Z is N.

14. A compound of claim 1 wherein X is N, Y is N and Z is C.

15. A compound of claim 1 wherein X is C, Y is N and Z is N.

16. A compound of claim 1 selected from the group consisting of:
    4,4-difluoro-piperidine-1-carboxylic acid [2-(4-cyclopentyl-piperazin-1-yl)-pyrimidin-4-yl]-amide,
    azepane-1-carboxylic acid [2-(4-cyclopentyl-piperazin-1-yl)-pyrimidin-4-yl]-amide,
    4-methyl-piperidine-1-carboxylic acid [6-(4-ethyl-piperazin-1-yl)-pyrimidin-4-yl]-amide,
    2-methyl-pyrrolidine-1-carboxylic acid [6-(4-ethyl-piperazin-1-yl)-pyrimidin-4-yl]-amide,
    3-methyl-piperidine-1-carboxylic acid [6-(4-ethyl-piperazin-1-yl)-pyrimidin-4-yl]-amide,
    1-cyclopentyl-3-[6-(4-ethyl-piperazin-1-yl)-pyrimidin-4-yl]-urea,
    piperidine-1-carboxylic acid [6-(4-isopropyl-piperazin-1-yl)-pyrimidin-4-yl]-amide,
    pyrrolidine-1-carboxylic acid [6-(4-isopropyl-piperazin-1-yl)-pyrimidin-4-yl]-amide,
    4-methyl-piperidine-1-carboxylic acid [6-(4-isopropyl-piperazin-1-yl)-pyrimidin-4-yl]-amide, and
    any pharmaceutically acceptable salt thereof.

17. A compound of claim 1 selected from the group consisting of:
azepane-1-carboxylic acid [6-(4-isopropyl-piperazin-1-yl)-pyrimidin-4-yl]-amide,
2-methyl-pyrrolidine-1-carboxylic acid [6-(4-isopropyl-piperazin-1-yl)-pyrimidin-4-yl]-amide,
3-methyl-piperidine-1-carboxylic acid [6-(4-isopropyl-piperazin-1-yl)-pyrimidin-4-yl]-amide,
1-cyclopentyl-3-[6-(4-isopropyl-piperazin-1-yl)-pyrimidin-4-yl]-urea,
2-methyl-pyrrolidine-1-carboxylic acid [6-(4-cyclopentyl-piperazin-1-yl)-pyrimidin-4-yl]-amide,
3-methyl-piperidine-1-carboxylic acid [6-(4-cyclopentyl-piperazin-1-yl)-pyrimidin-4-yl]-amide,
piperidine-1-carboxylic acid [6-(4-cyclohexyl-piperazin-1-yl)-pyrimidin-4-yl]-amide,
3-methyl-piperidine-1-carboxylic acid [6-(4-cyclohexyl-piperazin-1-yl)-pyrimidin-4-yl]-amide,
azepane-1-carboxylic acid [6-(4-cyclohexyl-piperazin-1-yl)-pyrimidin-4-yl]-amide,
and any pharmaceutically acceptable salt thereof.

18. A compound of claim 1 selected from the group consisting of:
2-methyl-piperidine-1-carboxylic acid [6-(4-cyclohexyl-piperazin-1-yl)-pyrimidin-4-yl]-amide,
4-methyl-piperidine-1-carboxylic acid [6-(4-cyclohexyl-piperazin-1-yl)-pyrimidin-4-yl]-amide,
octahydro-quinoline-1-carboxylic acid [6-(4-cyclohexyl-piperazin-1-yl)-pyrimidin-4-yl]-amide,
3,5-dimethyl-piperidine-1-carboxylic acid [6-(4-cyclohexyl-piperazin-1-yl)-pyrimidin-4-yl]-amide,
4-fluoro-piperidine-1-carboxylic acid [6-(4-cyclohexyl-piperazin-1-yl)-pyrimidin-4-yl]-amide,
1-cyclohexyl-3-[6-(4-cyclopentyl-piperazin-1-yl)-pyrimidin-4-yl]-1-isopropyl-urea,
piperidine-1-carboxylic acid [6-(4-cyclopentyl-piperazin-1-yl)-pyrimidin-4-yl]-amide,
pyrrolidine-1-carboxylic acid [6-(4-cyclopentyl-piperazin-1-yl)-pyrimidin-4-yl]-amide,
1,3-dihydro-isoindole-2-carboxylic acid [6-(4-cyclopentyl-piperazin-1-yl)-pyrimidin-4-yl]-amide, and
any pharmaceutically acceptable salt thereof.

19. A compound of claim 1 selected from the group consisting of:
1-cyclohexyl-3-[6-(4-cyclopentyl-piperazin-1-yl)-pyrimidin-4-yl]-urea,
azepane-1-carboxylic acid [6-(4-cyclopentyl-piperazin-1-yl)-pyrimidin-4-yl]-amide,
2-methyl-piperidine-1-carboxylic acid [6-(4-cyclopentyl-piperazin-1-yl)-pyrimidin-4-yl]-amide,
1-cyclopentyl-3-[6-(4-cyclopentyl-piperazin-1-yl)-pyrimidin-4-yl]-urea,
4-methyl-piperidine-1-carboxylic acid [6-(4-cyclopentyl-piperazin-1-yl)-pyrimidin-4-yl]-amide,
octahydro-quinoline-1-carboxylic acid [6-(4-cyclopentyl-piperazin-1-yl)-pyrimidin-4-yl]-amide,
4,4-difluoro-piperidine-1-carboxylic acid [6-(4-cyclopentyl-piperazin-1-yl)-pyrimidin-4-yl]-amide,
2,5-dihydro-pyrrole-1-carboxylic acid [6-(4-cyclopentyl-piperazin-1-yl)-pyrimidin-4-yl]-amide,
3,5-dimethyl-piperidine-1-carboxylic acid [6-(4-cyclopentyl-piperazin-1-yl)-pyrimidin-4-yl]-amide,
4-fluoro-piperidine-1-carboxylic acid [6-(4-cyclopentyl-piperazin-1-yl)-pyrimidin-4-yl]-amide, and
any pharmaceutically acceptable salt thereof.

20. A process for the manufacture of a compound of claim 1, which process comprises:
(a) reacting a compound of formula II:

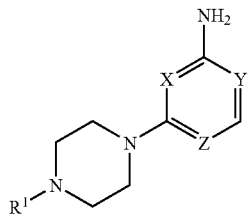

II wherein X, Y, Z and $R^1$ are as defined in claim 1,
with the chlorides of formula III:

$R^2$—C(O)Cl    III wherein $R^2$ is as defined in claim 1,
to obtain a compound of formula I-A:

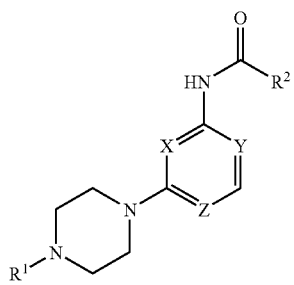

I-A wherein X, Y, Z, $R^1$ and $R^2$ are as defined in claim 1, and
(b) optionally converting a compound of formula I-A into a pharmaceutically acceptable salt.

21. A process for the manufacture of a compound of claim 1, which process comprises:
(a) activating a compound of formula II:

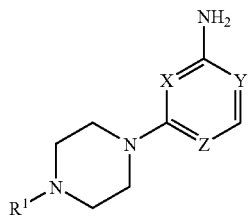

II wherein X, Y, Z and $R^1$ are as defined in claim 1,
with phenylchloroformates or di-tert-butyl dicarbonates to obtain carbamate esters of formula IV:

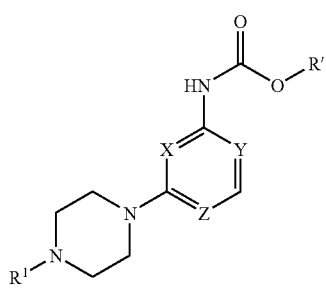

IV wherein R' is phenyl or tert-butyl, respectively, which is then reacted with amines of formula V:

H—NR³R⁴   V, wherein R³ and R⁴ are as defined in claim 1, to obtain a compound of formula I-B:

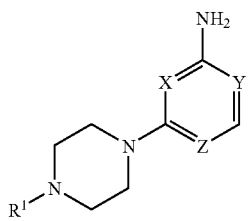

I-B wherein X, Y, Z, R¹, R³ and R⁴ are as defined in claim 1, and (b) optionally converting a compound of formula I-B into a pharmaceutically acceptable salt.

22. A process for the manufacture of a compound of claim 1, which process comprises:

(a) activating a compound of formula II:

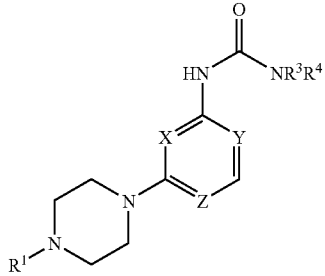

II wherein X, Y, Z and R¹ are as defined in claim 1, with the phenylchloroformates or di-tert-butyl dicarbonates to obtain the carbamate esters of formula IV:

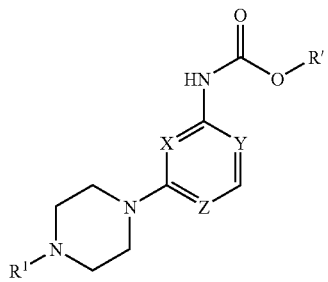

IV wherein R' is phenyl or tert-butyl, respectively, which is then reacted with the chlorides of formula III:

R²—C(O)Cl   III wherein R² is as defined in claim 1, to obtain a compound of formula I-C:

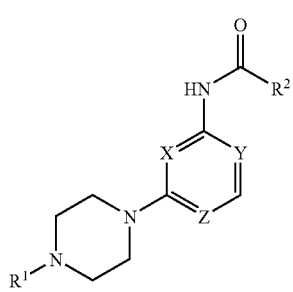

I-C wherein X, Y, Z, R¹ and R² are as defined in claim 1, and (b) optionally converting a compound of formula I-C into a pharmaceutically acceptable salt.

23. A pharmaceutical composition comprising a therapeutically effective amount of a compound of claim 1 and a pharmaceutically acceptable carrier.

* * * * *